US012569484B2

(12) United States Patent
Zhao et al.

(10) Patent No.: US 12,569,484 B2
(45) Date of Patent: Mar. 10, 2026

(54) USE OF PHOSPHODIESTERASE 5 INHIBITOR IN PREPARATION OF MEDICAMENT FOR RESISTING FIBROTIC DISEASES

(71) Applicant: SHENZHEN HANHUI PHARMACEUTICAL TECHNOLOGY CO., LTD., Guangdong (CN)

(72) Inventors: Allan Zijian Zhao, Guangdong (CN); Yunping Mu, Guangdong (CN); Fanghong Li, Guangdong (CN); Zhenggang Zhao, Guangdong (CN); Huidan Zhu, Guangdong (CN)

(73) Assignee: SHENZHEN HANHUI PHARMACEUTICAL TECHNOLOGY CO., LTD.., Guangdong (CN)

(*) Notice: Subject to any disclaimer, the term of this patent is extended or adjusted under 35 U.S.C. 154(b) by 973 days.

(21) Appl. No.: 17/776,012

(22) PCT Filed: Jul. 29, 2020

(86) PCT No.: PCT/CN2020/105561

§ 371 (c)(1),
(2) Date: Sep. 7, 2022

(87) PCT Pub. No.: WO2021/093376

PCT Pub. Date: May 20, 2021

(65) Prior Publication Data

US 2023/0233554 A1 Jul. 27, 2023

(30) Foreign Application Priority Data

Nov. 11, 2019 (CN) ......................... 201911096936.8

(51) Int. Cl.
*A61K 31/4985* (2006.01)
*A61K 9/00* (2006.01)
*A61K 31/52* (2006.01)
*A61P 11/00* (2006.01)

(52) U.S. Cl.
CPC ........ *A61K 31/4985* (2013.01); *A61K 9/0019* (2013.01); *A61K 31/52* (2013.01); *A61P 11/00* (2018.01)

(58) Field of Classification Search
CPC .................................................. A61K 31/4985
See application file for complete search history.

(56) References Cited

U.S. PATENT DOCUMENTS

| | | | | |
|---|---|---|---|---|
| 6,638,936 B1 * | 10/2003 | Briner | ..................... | A61P 43/00 514/254.11 |
| 10,912,778 B2 | 2/2021 | Weers et al. | | |
| 2008/0280914 A1 * | 11/2008 | Serno | ..................... | A61P 15/06 514/250 |
| 2016/0158233 A1 * | 6/2016 | Sandner | ............... | A61K 31/404 514/252.16 |

FOREIGN PATENT DOCUMENTS

| | | | |
|---|---|---|---|
| CN | 101102774 | A | 1/2008 |
| CN | 104069113 | A | 10/2014 |
| CN | 207970316 | U | 10/2018 |
| CN | 109157520 | A | 1/2019 |
| CN | 110381951 | A | 10/2019 |
| WO | 03063875 | A1 | 8/2003 |
| WO | 2004037183 | A2 | 5/2004 |
| WO | 2018/167142 | A1 | 9/2018 |

OTHER PUBLICATIONS

Decision of Refusal on corresponding Chinese application; Application No. 2019110969368.
Zahran. M.H. et al. "Renoprotective effect of local sildenafil administration in renal ischaemia-reperfusion injury: a randomised controlled canine study." Arab Journal of Urology, vol. 17. No. 2, Apr. 18, 2019 (Apr. 18, 2019) p. 150-159.

(Continued)

*Primary Examiner* — Rei Tsang Shiao
(74) *Attorney, Agent, or Firm* — DINSMORE & SHOHL LLP

(57) ABSTRACT

A phosphodiesterase type 5 inhibitor is used in the preparation of a medicament for resisting fibrotic diseases. Experiments in animal models of ischemia-reperfusion (UIRI)-induced renal fibrosis, unilateral ureteral obstruction (UUO)-caused kidney fibrosis and idiopathic pulmonary fibrosis show that a PDE5 inhibitor such as tadalafil, sildenafil and vardenafil can significantly inhibit the expression of multiple fibrosis iconic proteins such as fibronectin, collagen I, renal injury molecule-1, and α-skeletal muscle actin in UIRI and UUO renal fibrosis lesions, improves glomerulopathy, degree of renal tubular distension, renal interstitial collagen fiber deposition and inflammatory cell infiltration, reduces the fibrotic area within the lesion, and significantly inhibits the progression of renal fibrosis; and the PDE5 inhibitor can significantly improve smooth muscle proliferation and inflammatory cell infiltration in bronchioles and pulmonary arterioles of idiopathic pulmonary fibrosis lesion, improve damage condition of alveolar tissue, and significantly inhibit the progression of pulmonary fibrosis.

9 Claims, 9 Drawing Sheets

(56) References Cited

OTHER PUBLICATIONS

Cirrik. S. et al. "The Effect of Tadalafil on Renal Fibrosis Induced by Ureteral Obstruction." West Indian Medical Journal, vol. 68. No. 2, Jan. 25, 2017 (Jan. 25, 2017). p. 142-148.
Zimmermann. G.S. et al. "Haemodynamic changes in pulmonary hypertension in patients 1. 7-9. 14. 16-19. 29-33 with interstitial lung disease treated with PDE-5 inhibitors." Respirology, vol. 19. No. 5. Apr. 3, 2014 (Apr. 3, 2014). p. 700-706.
Cui. W.P. et al. "Increasing cGMP-dependent protein kinase activity attenuates unilateral ureteral obstruction-induced renal fibrosis." Am. J. Physiol. Renal Physiol., vol. 306, No. 9, Feb. 26, 2014 (Feb. 26, 2014), pp. F996-F1007.
International Search Report dated Oct. 29, 2020; International Application No. PCT/CN2020/105561.
Fang, Juan, Sildenafil Can Improve the Clinical Symptoms of Patients With Advanced Idiopathic Pulmonary Fibrosis, Natl Med J China. vol. 90, No. 36, p. 2548, published on Sep. 28, 2010.
Guo Jing wen, Research progress on therapeutic drugs for silicotic pulmonary fibrosis, Chinese J Ind Med, vol. 31 No.2, pp. 120-123, published on Apr. 30, 2018.
Zhou Wenhua, et al., ENHANCED cGMP-Dependent Protein Kinase Activity Alleviates Renal Fibrosis Due to Unilateral Ureteral Obstruction, Annual Congress of Chinese Society of Nephrol Ogy Poster Communication, p. 680, published on Dec. 31, 2014.
Sun Wei et al., Related research on the protective effect of tadalafil on renal function in rats with acute pyelonephritis, 2015 Zhejiang annual meeting of Urology andrology, pp. 133-134, published on: Jun. 27, 2015.
Mansour Heba M. et al, The anti-inflammatory and anti-fibrotic effects of tadalafil in thioacetamidc-induced liver fibrosis in rats, Icanadian Journal of Physiology and Pharmacology , vol. 96, No. 12, pp. 1308-1317, published on: Dec. 31, 2018.
Said Emanet al, Modulation of thioacetamidc-induced liver fibrosis/ treatment by sildenafil, Canadian Journal of Physiology and Pharmacology, 91 Volume, issue 12, pp. 1055-1063, published on: Dec. 31, 2013.
Limper, Andrew H. et al, Potential Role of Phosphodiesterase 5 Inhibitors in Decreasing Pulmonary Fibrosis Activity In Vitro, American Journal of Respiratory and Critical CareMedicine e, vol. 187, p. A3379, Dec. 31, 2013.
Chinese first office action dated Aug. 27, 2021, Chinese application No. 2019110969368.
Chinese third office action dated May 30, 2022; Chinese application No. 2019110969368.
Chinese second office action dated Feb. 24, 2022; Chinese application No. 201911069368.
Extended European Search Report dated Oct. 13, 2022; Application No. 20887883.5.
Zisman et al., A Controlled Trail of Sildenafil in Advanced Idiopathic Pulmonary Fibrosis; The New England Journal of Medicine; 9 pages.
Gong et al., Chronic inhibition of cyclic guanosine monophosphate-specific phosphodiesterase 5 prevented cardiac fibrosis through inhibition of transforming growth factor p-induced Smad signaling, Higher Education Press and Springer-Verlag Berlin Heidelberg 2014, 11 pages.
Higuchi et al., Sildenafil attenuates the fibrotic phenotype of skin fibroblasts in patients with systemic sclerosis, Institute of Rheumatology, Tokyo Women's Medical University, 10-22 Kawada-cho, Shinjuku-ku. Tokyo 162-0054, Japan, 6 pages.
Collard et al., Sildenafil Improves Walk Distance in Idiopathic Pulmonary Fibrosis, NIH Public Access Author Manuscript, published Mar. 2007, 897-899.
Polcari et al., Effect of the Phosphodiesterase-5 Inhibitor Zaprinast on Ischemia-Reperfusion Injury in Rats, Journal of Endourology vol. 27, No. 3, Mar. 2013, 5 pages.
Kyriazis et al., PDE5 inhibition against acute renal ischemia reperfusion injury in rats: does vardenafil offer protection?, Received: Jul. 17, 2012/Accepted: Oct. 25, 2012/Published online: Nov. 10, 2012, 6 pages.

* cited by examiner

USE OF PHOSPHODIESTERASE 5 INHIBITOR IN PREPARATION OF MEDICAMENT FOR RESISTING FIBROTIC DISEASES

CROSS-REFERENCE TO RELATED APPLICATIONS

This application is the U.S. National Stage of PCT/CN2020/105561 filed on Jul. 29, 2020, which claims priority to Chinese Patent Application 201911096936.8 filed on Nov. 11, 2019, the entire content of both are incorporated herein by reference in their entirety.

FIELD OF THE INVENTION

The present disclosure relates to the field of treatment of fibrotic diseases, and in particular, the present disclosure provides use of a phosphodiesterase type 5 inhibitor such as tadalafil and sildenafil in the manufacture of a medicament for treating a fibrotic disease, especially renal fibrosis and pulmonary fibrosis.

BACKGROUND OF THE INVENTION

Fibrosis refers to a pathological process in which necrosis of organ parenchymal cells, and abnormal increase and excessive deposition of an extracellular matrix in a tissue occur due to inflammation, which can occur in many major organs of a human body, including a liver, a lung, a kidney and a cardiovascular system. The main pathological changes include the increase of fibrous connective tissues in organ tissues, and the decrease of parenchymal cells, and mild cases develop into fibrosis. Continued progress can lead to organ structure destruction, hypofunction and even failure, which seriously threatens human health and life. It is reported that organ tissue fibrosis is a key cause of disability and death of many diseases in the whole country and even in the whole world. In the United States, nearly 45% of the patients who die from various diseases are attributed to tissue fibroplasia diseases.

A chronic kidney disease (CKD) is a chronic kidney dysfunction and structural change caused by many reasons, such as inflammation, ischemia reperfusion injury, obstruction, drugs, etc. The global prevalence rate is 14.5%, and it is increasing year by year. Renal fibrosis is a common pathological change in the progression of various CKDs to end-stage renal diseases, and it is a gradual process of a kidney function from health to injury, then to damage, until function loss. Although their pathogenic mechanisms are different, their main pathological features are all glomerular sclerosis and renal interstitial fibrosis that are caused by excessive deposition of the extracellular matrix, which exceeds the scavenging ability of the kidney. Meanwhile, fibroblasts are activated and accompanied by significant reduction of functional nephrons, resulting in irreversible pathological changes in the end stage of nephropathy, which is eventually developed into renal failure and death of a patient. It is another disease that seriously threatens public health after cancer, cardiovascular diseases, respiratory diseases and diabetes. Currently, there is no effective treatment method for renal fibrosis. Controlling risk factors, angiotensin-converting enzyme inhibitors, angiotensin receptor inhibitors and the like cannot stop the progress of the disease. The patient can only rely on lifelong dialysis or kidney transplantation to maintain his/her life, which brings a heavy economic burden to his/her family and society.

Therefore, there is an urgent need to develop a novel treatment strategy to delay the progress of CKD and reduce the harm of its complications, so as to improve the life quality of the patient and prolong the life expectancy of the patient.

An ideal animal model of renal fibrosis is of great significance to the research on the pathogenesis of CKD and the research and development of therapeutic drugs. Currently, the commonly used animal models of renal fibrosis by science researchers mainly include a drug or poison induced model, an operation model, and a genetic modification model, etc. Different models reflect different renal functions and pathological changes of renal tissues. Currently, the operations models for renal fibrosis that are more applied, include a unilateral renal ischemia-reperfusion injury model (UIRI), a unilateral ureteral obstruction model (UUO) and a 5/6 nephrectomy model (5/6NX). The UIRI is similar to clinical ischemia reperfusion injury such as renal transplantation and recanalization after renal vascular occlusion, which leads to irreversible damage of renal tissues and cell structures, resulting in renal tissue fibrosis. UUO is an ideal renal interstitial fibrosis model that simulates the renal interstitial injury caused by ureteral obstruction in clinic, which is manifested as collagen deposition, fibroplasia and inflammatory cell infiltration in renal interstitium. 5/6NX is simple in modeling, has high success rate, and is widely used since the occurrence of fibrosis is caused by residual renal compensation, hyperplasia of a glomerular matrix, sclerosis of renal tubules, and increase of the renal interstitium.

Idiopathic pulmonary fibrosis (IPF) is a chronic and progressive fiber proliferation pulmonary disease with main pathological changes in the disorders and disappearance of normal alveolar structures, the formation of a myofibroblast lesion and excessive deposition of an extracellular matrix, which eventually leads to irreversible loss of the lung function. According to the statistics, the incidence of IPF is about 6.8-16.3 cases/a population of 100,000, and with the gradual development of population aging, its incidence is constantly rising, and its global incidence has been progressively increased by about 11% every year in the recent 20 years. Currently, the etiology and pathogenesis of IPF are still unclear, and the onset age is not limited, but it mostly occurs in middle-aged and elderly patients, with poor prognosis. The median survival time after diagnosis is only 3-5 years, and the mortality rate even far exceeds those of many types of lung cancers. There is no specific medicament for IPF treatment. In recent years, a large number of clinical trials have confirmed that pirfenidone and nintedanib can delay the mild and moderate decline of the lung function and delay the survival time of a patient to a certain extent, but cannot reverse the aggravation of pulmonary fibrosis. Most of the patients still develop to respiratory failure and die within a few years. The IPF guideline of American College of Chest Physicians points out that lung transplantation may be the only recommended and effective treatment method for advanced IPF patients. However, the high surgical cost, complicated technology degree and scarce lung sources result in only a few patients being treated, and the immune rejection response after transplantation seriously limits its clinical application. The IPF has become a disease that seriously threatens human life and health, which has brought a heavy economic burden to patients' families and society. Therefore, it is an urgent problem for science researchers and clinicians in the respiratory field to find effective drug intervention measures to treat IPF clinically.

A phosphodiesterase (PDE) is an important hydrolase in an organism, can specifically catalyze the hydrolysis of cyclic guanosine monophosphate (cGMP) or cyclic adenosine monophosphate (cAMP) in cells to produce corresponding inactive 5'-nucleotides, thereby playing a biological role. cAMP and cGMP are two important second messengers in cells, and participate in various metabolic activities of the body by activating PKA and PKG pathways. The regulation of their intracellular concentrations is mainly determined by a balance between the synthesis of adenylate (guanylate) cyclase and the hydrolysis of PDE. PDEs are totally divided into 11 subtypes, widely distributed in a human body, and its physiological functions involve many research fields. Among them, phosphodiesterase type 5 (PDE5) has been studied most deeply, can specifically hydrolyze cGMP, and is mainly distributed in lung, pancreas, brain, corpus cavernosum of penis, vascular smooth muscle cells, platelets, skeletal muscle cells and cardiac muscle cells. A phosphodiesterase inhibitor is a medicament that inhibits the activities of PDEs. In recent years, many studies have gradually highlighted its role in diseases such as heart failure, hypertension, asthma, pulmonary arterial hypertension, diabetes, cerebrovascular diseases, Raynaud's diseases, erectile dysfunction and the like.

The existing PDE5 inhibitors mainly include tadalafil, sildenafil, vardenafil and the like. Sildenafil, a first PDE5 inhibitor approved by FDA, is currently a first-line medicament for clinical treatment of erectile dysfunction. By selectively inhibiting PDE5, preventing the degradation of cGMP, and increasing the level of cGMP in cells, the role of nitric oxide in relaxing vascular smooth muscle and reducing vascular resistance can be improved. Since the listing of sildenafil, tadalafil and vardenafil have also been successively listed. The PDE5 inhibitors that have been developed or are being developed mainly target diseases such as erectile dysfunction, cardiovascular diseases, diabetes, cerebrovascular diseases, and the like. Some studies have showed that sildenafil can inhibit myocardial fibrosis and myocardial hypertrophy and improve a cardiac function in an animal model; sildenafil combined with pirfenidone may have a positive effect on patients with advanced IPF complicated with pulmonary hypertension; sildenafil significantly improves the exercise ability and life quality of patients with IPF complicated with right heart dysfunction; and there is no definite research conclusion on the therapeutic effect of a specific phosphodiesterase type 5 inhibitor on the fibrotic disease, especially renal fibrosis and pulmonary fibrosis, and no corresponding medicaments are listed.

SUMMARY OF THE INVENTION

In order to develop a new type of medicaments for resisting a fibrotic disease, especially renal fibrosis and pulmonary fibrosis, while expanding the use of existing medicaments such as tadalafil, sildenafil, vardenafil, etc., the applicant uses male BALB/c mice to perform unilateral renal ischemia-reperfusion surgery (UIRI) to induce an animal model of renal fibrosis and study the pathophysiological effects of a PDE5 inhibitor, a sildenafil analog CPD1. The experiments have confirmed that the PDE5 inhibitor inhibits the increase in expression amount of fibronectin (FN) and plasminogen activator inhibitor-1 (PAI-1) in renal interstitial fibroblasts (NRK-49F) induced by TGF-β in a concentration-dependent manner, significantly improves the activation and collagen deposition of renal myofibroblasts in the lesion of the UIRI mice, and significantly reduces the expression of FN, collagen I, PAI-1 and α-sarcometric actin (α-SMA) in renal tissues. The pathophysiological effects of the PDE5 inhibitor tadalafil, are studied by utilizing C57BL/6 wild-type mice to perform unilateral ureteral ligation operation (UUO) to induce a classic animal model of renal fibrosis. The experiments have confirmed that the PDE5 inhibitor inhibits the expression of FN, collagen I, a kidney injury molecule-1 (Kim-1) and α-SMA in renal tissues in a concentration-dependent manner, improves the damage of glomerular and tubular structures in a renal fibrosis lesion, significantly reduces the fibrotic area in the lesion, and inhibits the development of renal fibrosis. The pathophysiological effects of the PDE5 inhibitors tadalafil and sildenafil are studied by intratracheal injection of bleomycin in SD rats as a model of idiopathic pulmonary fibrosis. The experiments have confirmed that the PDE5 inhibitor obviously improves the smooth muscle proliferation, inflammatory cell infiltration and alveolar tissue injury of bronchioles and pulmonary arterioles in the fibrotic lesion of rats with idiopathic pulmonary fibrosis, and significantly inhibits the progression of pulmonary fibrosis.

On this basis:

in one aspect, the present disclosure provides use of a phosphodiesterase type 5 inhibitor in the manufacture of a medicament for treating a fibrotic disease.

Further, the fibrotic disease is renal fibrosis.

Further, the fibrotic disease is renal fibrosis caused by renal ischemia-reperfusion injury.

Further, the phosphodiesterase type 5 inhibitor is a sildenafil analog CPD1.

Further, the fibrotic disease is renal fibrosis caused by ureteral obstruction.

Further, the phosphodiesterase type 5 inhibitor is tadalafil.

Further, the fibrotic disease is pulmonary fibrosis.

Further, the fibrotic disease is idiopathic pulmonary fibrosis.

Further, the phosphodiesterase type 5 inhibitor is tadalafil and/or sildenafil.

Further, the fibrosis is cardiac fibrosis or hepatic fibrosis.

In another aspect, the present disclosure provides use of a phosphodiesterase type 5 inhibitor in the manufacture of a medicament for reducing a level of FN1, Collagen I, Kim-1, PAI-1 and/or α-SMA in a kidney tissue.

Further, ischemia reperfusion injury occurs in the kidney tissue.

Further, obstruction occurs in the kidney tissue.

In another aspect, the present disclosure provides a pharmaceutical composition for treating a fibrotic disease, including a phosphodiesterase type 5 inhibitor and a pharmaceutically-acceptable auxiliary material or excipient.

Further, the fibrotic disease is renal fibrosis caused by ischemia reperfusion injury, and the phosphodiesterase type 5 inhibitor is a sildenafil analog CPD1.

Further, the fibrotic disease is renal fibrosis caused by ureteral obstruction, and the phosphodiesterase type 5 inhibitor is tadalafil.

Further, the fibrotic disease is idiopathic pulmonary fibrosis, and the phosphodiesterase type 5 inhibitor is tadalafil and/or sildenafil.

In the aforementioned use/pharmaceutical composition, the medicament can be in an oral, injection or atomized dosage form.

Besides the aforementioned fibrosis types, the fibrosis in the present disclosure can also be fibrosis in other tissues and organs, including but not limited to vascular fibrosis, spleen fibrosis, multiple sclerosis, etc.

In addition to tadalafil and sildenafil, the phosphodiesterase type 5 inhibitor in the present disclosure also includes existing or developing phosphodiesterase type 5 inhibitors such as vardenafil, and those skilled in the art can study and verify their properties before they are used in the use of the present disclosure.

The oral, injection or atomized dosage forms of the present disclosure include various specific dosage forms, including but not limited to tablets, capsules, oral liquid, injections, powder injections, etc. Besides the oral, injection or atomized dosage forms, those skilled in the art can also design other dosage forms as desired, including but not limited to a dosage form suitable for external use, etc.

According to the needs of dosage forms and common knowledge of pharmaceutics, the prepared medicament can contain various pharmaceutically-acceptable auxiliary materials and excipients, including but not limited to coating materials, solvents, solubilizers, adhesives, stabilizers, antioxidants, pH regulators, correctants, etc.

Other known medicaments for treating or relieving fibrosis can also be included in the medicament of the present application, including but not limited to a TGF-β inhibitor, a renin/angiotensin regulator, a calcium channel regulator, an angiogenesis inhibitor, a relaxin derivative, an erythropoietin derivative, a steroidal or nonsteroidal anti-inflammatory medicament, other hormone drugs and traditional Chinese medicine compositions.

In another aspect, the present disclosure provides a method for treating a fibrotic disease, including administering a phosphodiesterase type 5 inhibitor to a subject in need thereof.

Further, the fibrotic disease is renal fibrosis.

Further, the fibrotic disease is renal fibrosis caused by renal ischemia reperfusion injury.

Further, the fibrotic disease is renal fibrosis caused by ureteral obstruction.

Further, the phosphodiesterase type 5 inhibitor is a sildenafil analog CPD1.

Further, the phosphodiesterase type 5 inhibitor is tadalafil.

Further, the sildenafil analog CPD1 is orally administrated at a dosage of 0.405 $mg \cdot kg^{-1} \cdot d^{-1}$ for 10 days.

Further, the sildenafil analog CPD1 is administrated by injection at a dosage of 0.1215-0.162 $ml \cdot kg^{-1} \cdot d^{-1}$ for 10 days.

Further, the tadalafil is orally administrated at a dosage of 0.081-0.81 $mg \cdot kg^{-1} \cdot d^{-1}$ for 7 days.

Further, the tadalafil is administrated by injection at a dosage of 0.0243-0.324 $ml \cdot kg^{-1} \cdot d^{-1}$ for 7 days.

Further, the fibrotic disease is pulmonary fibrosis.

Further, the fibrotic disease is idiopathic pulmonary fibrosis.

Further, the phosphodiesterase type 5 inhibitor is tadalafil or sildenafil.

Further, the tadalafil is orally administrated at a dosage of 0.81-3.24 $mg \cdot kg^{-1} \cdot d^{-1}$ for 14 days; or the sildenafil is orally administrated at a dosage of 3.24 $mg \cdot kg^{-1} \cdot d^{-1}$ for 14 days.

Further, the tadalafil is administrated by injection at a dosage of 0.243-1.296 $ml \cdot kg^{-1} \cdot d^{-1}$ for 14 days; or the sildenafil is administrated by injection at a dosage of 0.972-1.296 $ml \cdot kg^{-1} \cdot d^{-1}$ for 14 days.

Further, the fibrosis is cardiac fibrosis or hepatic fibrosis.

The selective PDE5 inhibitors tadalafil, sildenafil and sildenafil analog CPD1 of the present disclosure can obviously improve the cell activation and collagen deposition of myofibroblasts in UIRI and UUO renal fibrosis lesions, inhibit the expression of multiple fibrosis iconic proteins in the UIRI and UUO renal fibrosis lesions, improve the damage of glomerular and renal tubular structures and inhibit the development of renal fibrosis; obviously improve the smooth muscle proliferation and inflammatory cell infiltration in bronchioles and pulmonary arterioles of idiopathic pulmonary fibrosis lesion, and damage conditions of alveolar tissue, and significantly inhibit the progression of pulmonary fibrosis. It indicates that the PDE5 inhibitor is expected to become an important target in the research of resisting fibrotic diseases, which provides a foundation for the preparation of anti-fibrosis medicaments and has a good development and application prospect.

DETAILED DESCRIPTION OF THE INVENTION

Figure 1:
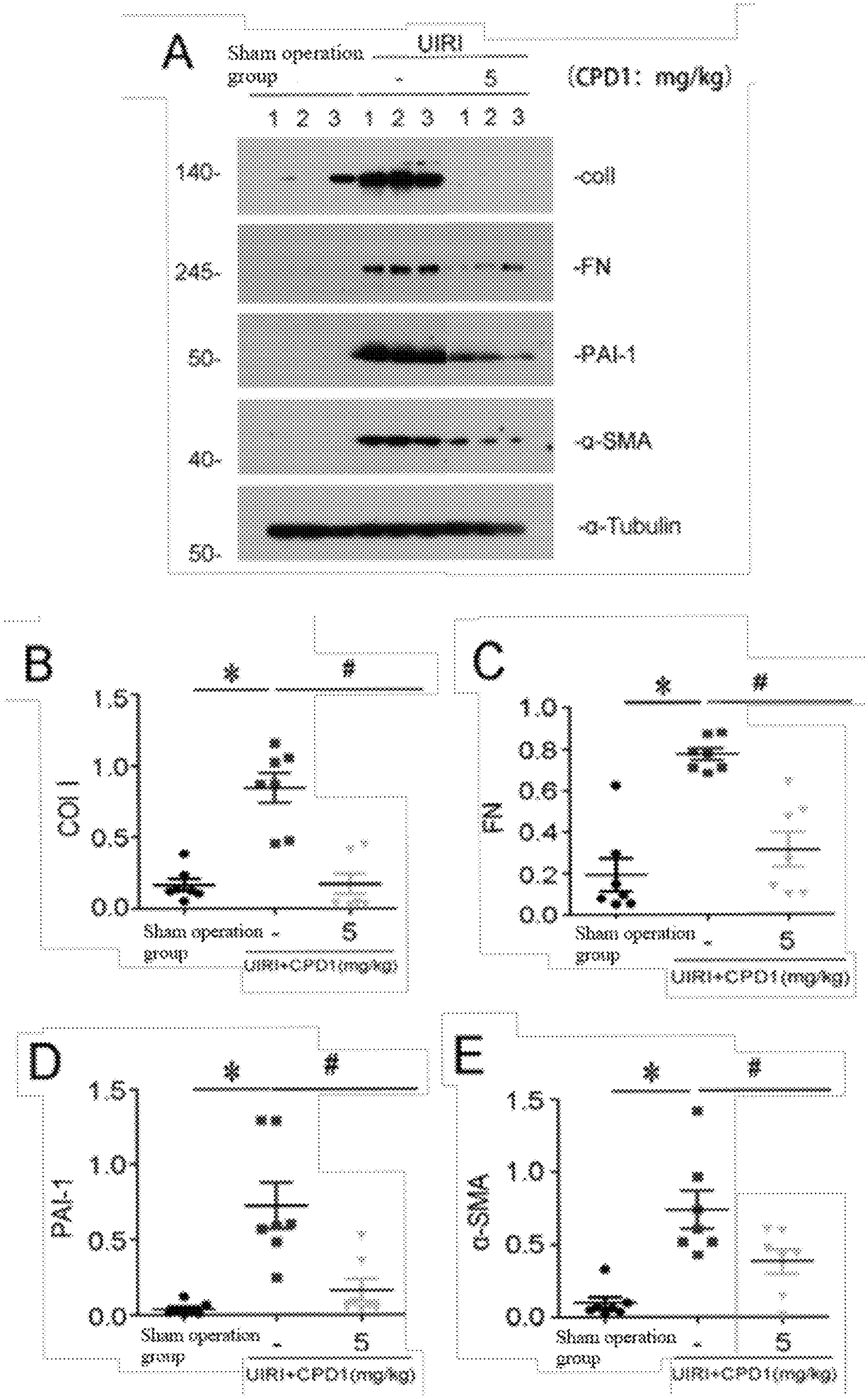
FIG. 1 shows that a PDE5 inhibitor CPD1 can improve the renal fibrosis of mice in a UIRI model in vivo, wherein A is an immunoblotting standard diagram of inhibiting the expression of FN, Collagen I, PAI-1 and α-SMA proteins in renal fibrosis lesions by CPD1, the numbers (1, 2, 3) represent each animal in each group, and B-E are statistical diagrams of determined relative contents of FN, collagen I, PAI-1 and α-SMA.

The following examples are provided for a better understanding of the present disclosure, and are not limited to the best embodiments and do not limit the content and protection scope of the present disclosure. Any product that is the same as or similar to the present disclosure, that is obtained by anyone under the inspiration of the present disclosure or by combining the present disclosure with other features of the prior art, is within the protection scope of the present disclosure.

Example 1: Effect of a PDE5 Inhibitor Sildenafil Analog CPD1 on UIRI Renal Fibrosis Model Mice 1. Experimental Materials 1.1 Reagents Fetal bovine serum and a DMEM/F12 medium were purchased from Gibco, USA, TGF-beta1: Minneapolis, USA, a mouse anti-α-SMA antibody, a mouse anti-α-tubulin antibody, a rabbit anti-Fibronectin antibody and sodium carboxymethyl cellulose were products of Sigma Reagent Company, USA; a rabbit anti-collagen-I antibody, and a rabbit anti-Kim-1 antibody were purchased from Millipore, USA; anti-rabbit and anti-mouse secondary antibodies were purchased from Jackson, USA; a compound PDE5 inhibitor sildenafil analog CPD1 was purchased from Apptec Co., Ltd.; and isoflurane, a pentobarbital sodium anesthetic and formalin were purchased from Sinopharm Group Co., Ltd., China.

1.2 Instruments

Carbon dioxide incubator: Heraeus, Germany; an optical microscope camera system available from Nikon, Japan; a benchtop high speed refrigerated centrifuge: Thermo, USA; a tissue hydroextractor: HistoCore Pearl, Leica; an embedding machine: HistoCore Arcadia, Leica; a slicer: RM2235, Leica; an automatic staining machine: LEICA Autostainer ST5020; a slice scanner: Hamamatsu NanoZoomer Digital Pathology (S210); an analytical balance: Precia, Germany; a weight scale: Changshu G&G Measurement Plant, T1000; an operation microscope: Luckbird XTS-4A; a gel imaging system: Bio-Rad, USA; an electrophoresis tank and an electrophoresis apparatus: Bio-Rad, USA; a pH instrument: ETTLER, Switzerland.

1.3 Experimental Animals

SPF-grade male BALB/c mice, weighed about 20 g. The mice were purchased from Laboratory Animal Center of Southern Medical University, with the license number: SCXK (Guangdong)-2011-0015. During the experiment process, the animals were treated in strict accordance with the Guidance Suggestions for the Care and Use of Laboratory Animals issued in 2006.

1.4 Experimental Cells

The normal rat kidney fibroblasts (NRK-49F) were induced by TGF-β, and the effect of a PDE5 inhibitor on the activation of NRK-49F cells was observed.

2. Experimental Methods 2.1 UIRI Model (Mouse Unilateral Renal Ischemia-Reperfusion Model)

2.1.1 Modeling and Grouping 15 male BALB/c mice were fed adaptively for one week, and randomly divided into two groups: a Sham group (a sham operation group) with 5 mice and an operation modeling group with 10 mice. Operation method: after anesthesia, the mice were fixed on an operating board in a supine position and subjected to skin preparation, an incision of about 1.5 cm was cut off in the left abdomen to expose the kidney, and blunt dissection of a renal pedicle was conducted. In the sham operation group, the renal pedicle was only exposed without clamping; in the modeling group, the renal pedicle of the left kidney was clamped for 30 min with a noninvasive micro-artery clamp. During the clamping, the mice were placed on a plate at a constant temperature of 37° C. to keep their body temperatures constant, and the surgical incisions were covered with gauze soaked with normal saline to prevent dehydration of the renal tissues. After 30 min, the arterial clamp was removed, and it was observed that the kidney gradually changed from purple-black to bright red within 1 min, indicating that blood flow reperfusion was successful. Finally, the kidney was put back in place and the wound was sutured. The mice in the modeling group were randomly divided into 2 groups: a UIRI group (a model group) and a CPD1 treatment group (5 mg/kg), with 5 mice in each group.

2.1.2 Administration

The first administration was started 2 hours after operation by adopting an intragastric administration manner.

(i) Sham group and UIRI model group: the mice were given normal saline by intragastric administration according to their body weights at a dosage of 0.1 ml·10 $g^{-1}·d^{-1}$;

(ii) CPD1 treatment group: CPD1 was diluted into a solution of 1 mg/ml with normal saline, and administrated intragastrically at a dosage of 5 $mg·kg^{-1}·d^{-1}$; and the administration was conducted once a day for 10 days in total.

(1) according to an interspecific dosage conversion method currently adopted by FDA, USA, the conversion coefficient of mice and human was 0.081. Therefore, according to the dosage and time of intragastric administration of CPD1 to the mice in this example, it was inferred that the oral dosage of human was 0.405 $mg·kg^{-1}·d^{-1}$, and the administration time was 10 days.

(2) according to dosage conversion among different routes of administration in pharmacological experimental methodology, a dosage ratio of intramuscular injection and intraperitoneal injection to oral administration was about 0.3-0.4, so it was inferred that the injection dosage of CPD1 in human was 0.1215-0.162 $ml·kg^{-1}·d^{-1}$, and the administration time was 10 days (medicament concentration: 1 mg/ml).

2.2 Specimen Collection and Processing

On day 10 after operation, the mice were anesthetized by the same method, the right backs of the mice were cut open to expose right kidneys, and the right kidneys were cut off after ligation of renal pedicles. In the sham operation group, only renal capsules were stripped from the mice, and the right kidneys were not cut off. On day 11 after operation, all the mice were sacrificed, abdominal cavities were opened to strip left kidney tissues of the mice, and Care should be taken to maintain the integrity of the kidneys. After the kidneys were taken out, they were quickly transferred into pre-cooled PBS, and the kidneys were cut for different tests. The kidney was divided into four parts by a scalpel. The ventral upper and lower poles of the kidney were placed in liquid nitrogen for extraction of proteins and mRNAs, and the changes in the expression amount of proteins and genes of fibrosis-related factors were detected. After 2 hours, the kidney tissues were transferred into a refrigerator of −80° C. for cryopreservation. The back side of the kidney was fixed in 4% paraformaldehyde, which was used for making paraffin sections. The paraffin sections were subjected to HE staining and Masson staining to observe the morphological changes of the kidney tissues, and the change of the expression amount of fibrosis iconic proteins in the kidney tissues was observed by immunohistochemistry.

2.3 Culture and Treatment of Fibroblasts (NRK-49F)

A normal rat kidney fibroblast cell line (NRK-49F) was subcultured in a DMEM/F12 medium (containing 10% FBS) at 37° C. in a 5% carbon dioxide incubator until a confluence of about 50% was reached, and then was continued to be subjected to starvation culture for 12 hours for follow-up experiments. Experimental grouping: (i) a blank control group: incubation in a serum-free DMEM medium for 48 hours; (ii) a CPD1 group: incubation in a serum-free DMEM medium containing 100 μM CPD1 (dissolved in normal saline) for 1 hour; (iii) a TGF-β group: incubation in a serum-free DMEM medium containing 10 ng/ml of TGF-β for 48 hours; and (iv) a TGF-β+CPD1 group: pre-incubation in different concentrations of CPD1 (10 UM, 20 μM, 40 μM, 60 μM, 80 μM, 100 μM) for 1 hour, and incubation in a serum-free DMEM medium containing 10 ng/ml of TGF-β for 48 hours after replacement of the medium.

3. Experimental Results 3.1 the PDE5 Inhibitor CPD1 Significantly Reduced the Expression of FN1, Collagen I, PAI-1 and α-SMA in the Kidney Tissues of the UIRI Mice.

The Western Blot results showed (FIG. 1) that in the kidney tissues of the mice, the expression of fibrosis iconic factors FN1, Collagen I, PAI-1 and α-SMA proteins was very low under a basic state, and their expression amounts in the kidney tissues of the UIRI model mice were significantly increased, while in the group administrated with CPD1 for prevention, the expression levels of these proteins were significantly decreased. It was indicated that the PDE5 inhibitor could inhibit the formation of renal fibrosis induced by ischemia reperfusion injury.

3.2 the PDE5 Inhibitor CPD1 Effectively Alleviated the Renal Fibrosis Lesions in the UIRI Mice.

Figure 2:
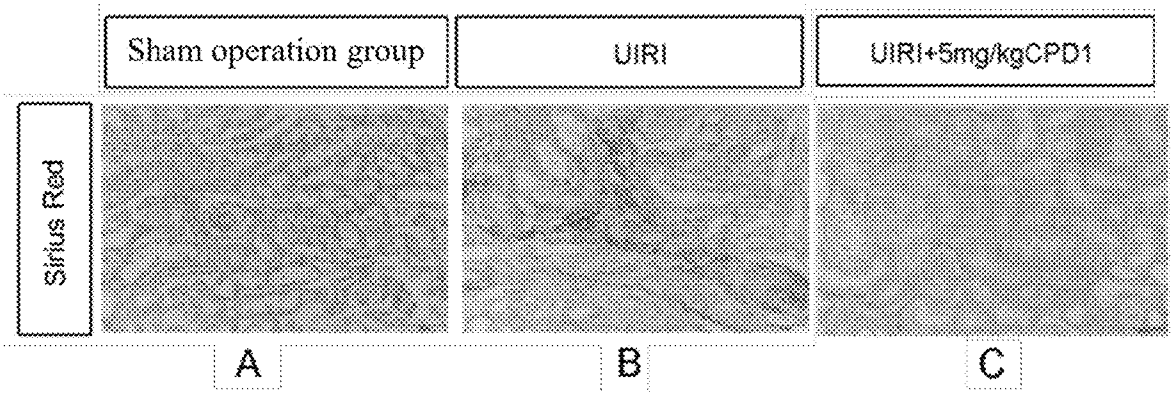
FIG. 2 shows a comparison diagram (HE staining) of changes of glomerular and renal tubular tissue structures in left renal fibrosis lesions after treatment of mice in a UIRI model by a PDE5 inhibitor for ten days, wherein A-C respectively represent a sham operation group, a UIRI model group and a CPD1 treatment group.
Figure 3:
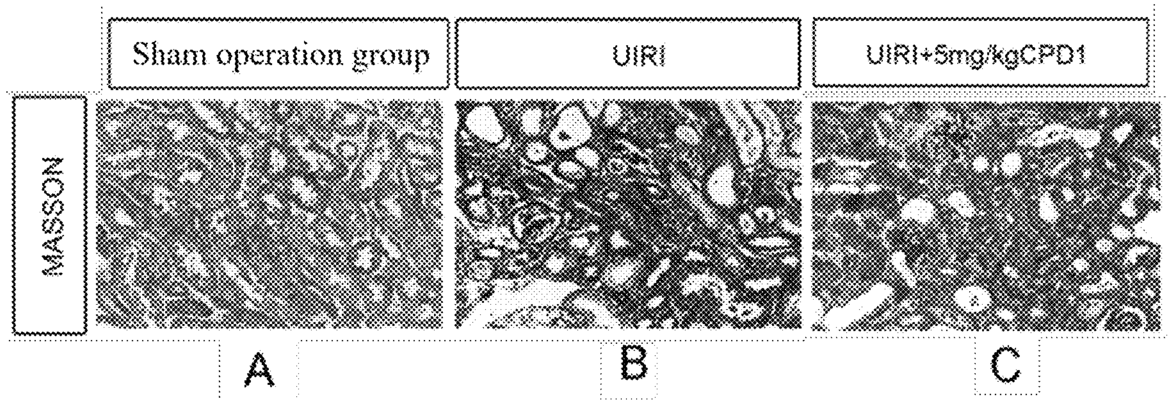
FIG. 3 shows a comparison diagram (Masson Trichrome staining) of changes of glomerular and renal tubular tissue structures in left renal fibrosis lesions after treatment of mice in a UIRI model by a PDE5 inhibitor for ten days, wherein A-C respectively represent a sham operation group, a UIRI model group and a CPD1 treatment group.
Figure 4:
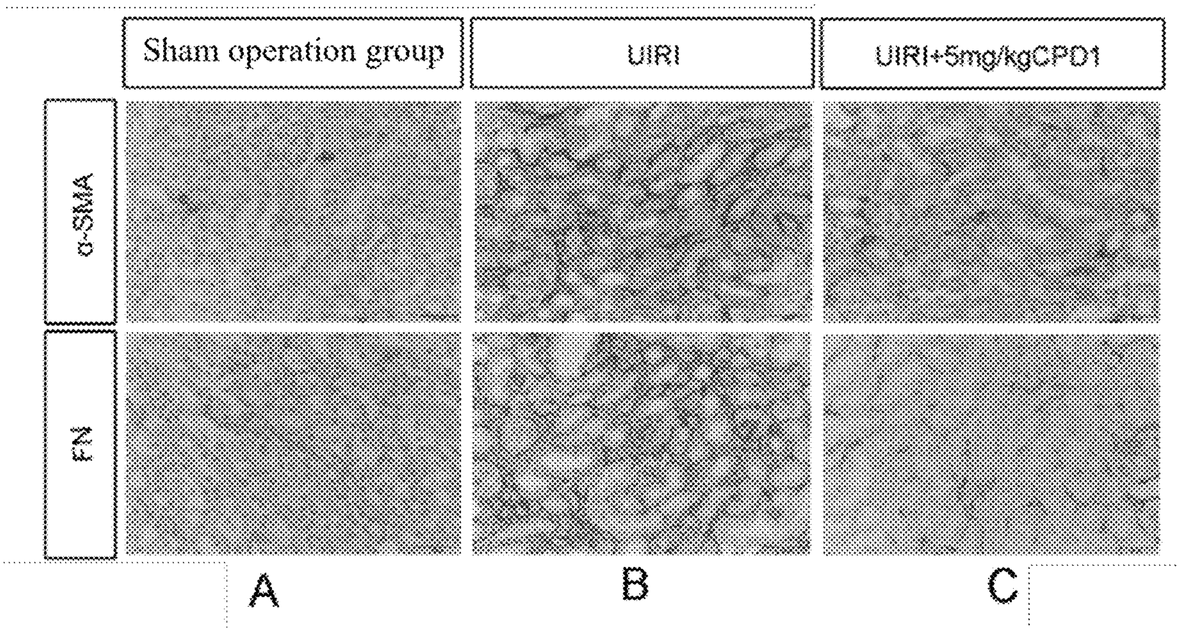
FIG. 4 shows the changes (immunohistochemistry) of the expression amount of FN and α-SMA in renal fibrosis lesions after mice in a UIRI model are treated with a PDE5 inhibitor for ten days, wherein A-C represent a sham operation group, a UIRI model group and a CPD1 treatment group respectively.

The results of HE staining (FIG. 2) and Masson staining (FIG. 3) showed that in the mice of the sham operation group, the structures of kidney tissues were normal, the glomerulus was not atrophied, and there were no pathological changes such as renal tubular dilatation, inflammatory cell infiltration and interstitial fibrous tissue proliferation. Compared with the mice of the sham operation group, in the mice of the UIRI operation group, the renal tissue and cell structures were irreversibly damaged, the renal tubules were atrophied or disappeared, glomerular sclerosis occurred, collagen fibers in the renal interstitium were significantly increased, collagen deposition was significant, and interstitial inflammatory cells were infiltrated to cause fibrosis. The immunohistochemical (FIG. 4) results showed that FN1 and α-SMA proteins secreted by myofibroblasts were significantly increased in the renal fibrosis lesions of the UIRI mice. After CPD1 treatment, in the kidney, the infiltration of inflammatory cells was significantly decreased, the deposition of the extracellular matrix was significantly decreased, and the expression levels of FN1 and α-SMA proteins were also decreased significantly.

3.3 in the NRK-49F Cells, the PDE5 Inhibitor CPD1 Inhibited the Expression of FN1 and PAI-1 Proteins Induced by TGF-β in a Dose-Dependent Manner.

Figure 5:
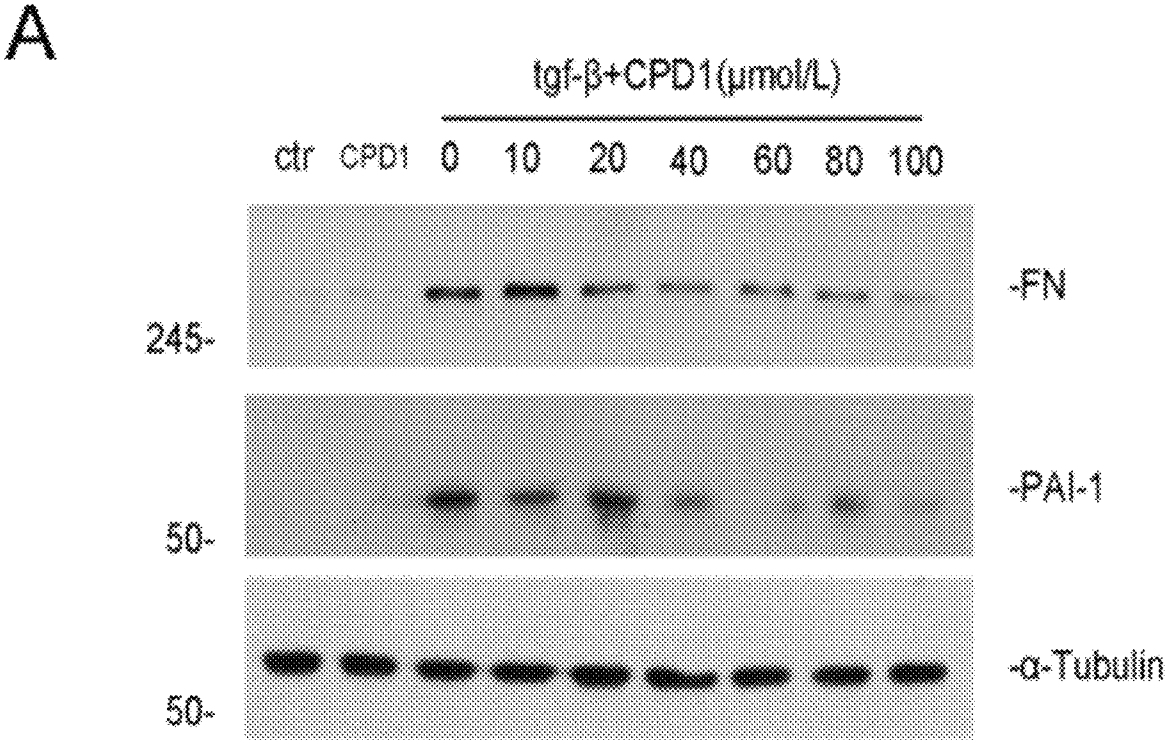
FIG. 5 shows the effect of different dosages of a PDE5 inhibitor on the expression of FN1 and PAI-1 proteins in NRK-49F cells induced by TGF-β.

The Western Blot results showed (FIG. 5) that the expression of FN1 and PAI-1 proteins in the NRK-49F cells was very low under the basic state, and their expression levels were significantly increased after TGF-β pure stimulation, while the expression of these proteins could be significantly inhibited by adding different concentrations of CPD1 in advance, and showed a concentration-dependent trend. It was indicated that the PDE5 inhibitor could effectively inhibit the activation of renal fibroblasts induced by TGF-β.

Example 2: Effect of a PDE5 Inhibitor Tadalafil on UUO Renal Fibrosis Model Mice 1. Experimental Materials 1.1 Reagents A α-SMA primary antibody and sodium carboxymethylcellulose were products of Sigma Reagent Company, USA; a Fibronectin primary antibody, Collagen-I, and a Kim-1 primary antibody, were purchased from Millipore, USA; anti-rabbit and anti-mouse secondary antibodies were purchased from Invitrogen, USA; a compound PDE5 inhibitor tadalafil was purchased from Apptec Co., Ltd.; and isoflurane, a pentobarbital sodium anesthetic and formalin were purchased from Sinopharm Group Co., Ltd., China.

1.2 Instruments an optical microscope camera system available from Nikon, Japan; a benchtop high speed refrigerated centrifuge: Thermo, USA; a tissue hydroextractor: HistoCore Pearl, Leica; an embedding machine: HistoCore Arcadia, Leica; a slicer: RM2235, Leica; an automatic staining machine: LEICA Autostainer ST5020; a slice scanner: Hamamatsu NanoZoomer Digital Pathology (S210); an analytical balance: Precia, Germany; a weight scale: Changshu G&G Measurement Plant, T1000; an operation microscope: Luckbird XTS-4A; a gel imaging system: Bio-Rad, USA; an electrophoresis tank and an electrophoresis apparatus: Bio-Rad, USA; a pH instrument: ETTLER, Switzerland.

1.3 Experimental Animals

SPF-grade male C57BL/6 mice, weighed about 20 g. The mice were purchased from Laboratory Animal Center of Southern Medical University, with the license number: SCXK (Guangdong)-2011-0015. During the experiment process, the animals were treated in strict accordance with the Guidance Suggestions for the Care and Use of Laboratory Animals issued in 2006.

2. Experimental Methods 2.1 UUO Model (Mouse Unilateral Ureteral Obstruction Model)

2.1.1 Modeling and Grouping 25 male C57BL/6 mice were fed adaptively for one week, and randomly divided into two groups: a Sham group (a sham operation group) with 5 mice and an operation modeling group with 20 mice. Operation method: for the mice in the sham operation group, the abdominal cavity was opened to free a left ureter without ligation under an anesthesia state, and the abdomen was closed and sutured; and for the mice in the modeling group, a left ureter was ligated under an anesthesia state. The mice in the modeling group were randomly divided into 4 groups: a UUO group (a model group), a tadalafil low-dosage group (1 mg/kg), a tadalafil medium-dosage group (3 mg/kg) and a tadalafil high-dosage group (10 mg/kg), with 5 mice in each group.

2.1.2 Administration

The first administration was started 2 hours after operation by adopting an intragastric administration manner.

(i) Sham group and UUO model group: the mice were given normal saline by intragastric administration according to their body weights at a dosage of 0.1 ml·10 $g^{-1}·d^{-1}$;

(ii) tadalafil-1 mg/kg group: tadalafil was diluted into a 0.2 mg/ml solution with 0.5% sodium carboxymethylcellulose, and administrated intragastrically at a dosage of 1 $mg·kg^{-1}·d^{-1}$;

(iii) tadalafil-3 mg/kg group: tadalafil was diluted into a 1 mg/ml solution with 0.5% sodium carboxymethylcellulose, and administrated intragastrically at a dosage of 3 $mg·kg^{-1}·d^{-1}$;

(iv) tadalafil-10 mg/kg group: tadalafil was diluted into a 2 mg/ml solution with 0.5% sodium carboxymethylcellulose, and administrated intragastrically at a dosage of 10 $mg·kg^{-1}·d^{-1}$; and the administration was conducted once a day for 7 days in total.

(1) according to an interspecific dosage conversion method currently adopted by FDA, USA, the conversion coefficient of mice and human was 0.081. Therefore, according to the dosage and time of intragastric administration of tadalafil to the mice in this example, it was inferred that the oral dosage of human was 0.081-0.81 $mg·kg^{-1}·d^{-1}$ and the administration time was 7 days.

(2) according to dosage conversion among different routes of administration in pharmacological experimental methodology, a dosage ratio of intramuscular injection and intraperitoneal injection to oral administration was about 0.3-0.4, so it was inferred that the injection dosage of tadalafil in human was 0.0243-0.324 $ml·kg^{-1}·d^{-1}$, and the administration time was 7 days (medicament concentration: 1 mg/ml).

2.2 Specimen Collection and Processing

After 7 days of administration, all the mice were sacrificed, abdominal cavities were opened to strip the left and right kidney tissues of the mice, and Care should be taken to maintain the integrity of the kidney. After the kidney was taken out, it was quickly transferred into pre-cooled PBS, and the kidney was cut for different tests. The kidney was divided into four parts by a scalpel. The ventral upper and lower poles of the kidney were placed in liquid nitrogen for extraction of proteins and mRNAs, and the changes in the expression amount of proteins and genes of fibrosis-related factors were detected. After 2 hours, the kidney tissues were transferred into a refrigerator of −80° C. for cryopreservation. The back side of the kidney was fixed in 4% paraformaldehyde, which was used for making paraffin sections. The paraffin sections were subjected to HE staining and Masson staining to observe the morphological changes of the kidney tissues, and the change of the expression amount of fibrosis iconic proteins in the kidney tissues was observed by immunohistochemistry.

3. Experimental Results 3.1 the PDE5 Inhibitor Tadalafil Significantly Reduced the Expression of FN1, Collagen I, Kim-1 and α-SMA in the Kidney Tissues of the UUO Mice.

Figure 6:
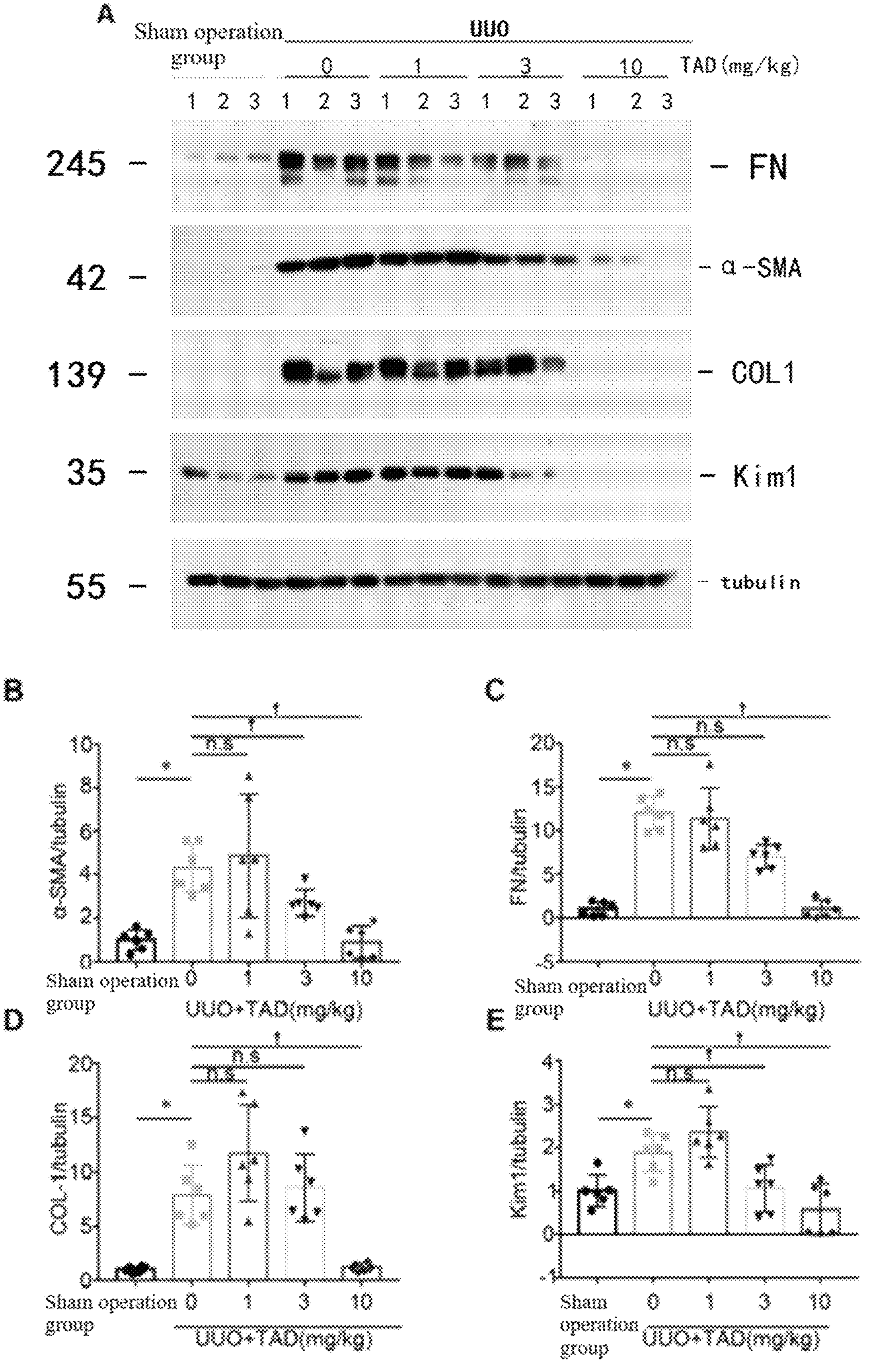
FIG. 6 shows that different dosages of a PDE5 inhibitor tadalafil can significantly improve the renal fibrosis of mice in a UUO model in vivo, wherein A is an immunoblotting standard diagram of inhibiting the expression of FN, collagen I, Kim-1 and α-SMA proteins in renal fibrosis lesions by different dosages of tadalafil, the numbers (1, 2, 3) represent each animal in each group, and B-E are statistical diagrams of determined relative contents of FN, collagen I, Kim-1 and α-SMA.

The Western Blot results showed (FIG. 6) that the expression of FN1, Collagen I, PAI-1 and α-SMA proteins in the kidney tissues of the mice was very low under a basic state, and their expression levels in the kidney tissues of the UUO model mice were all significantly increased, while in the group administrated with different concentrations of tadalafil for prevention, the expression levels of these proteins were significantly decreased. It was indicated that tadalafil could inhibit the formation of renal fibrosis in a dose-dependent manner.

3.2 the PDE5 Inhibitor Tadalafil Effectively Alleviated the Renal Fibrosis Lesions in the UUO Mice.

Figure 7:
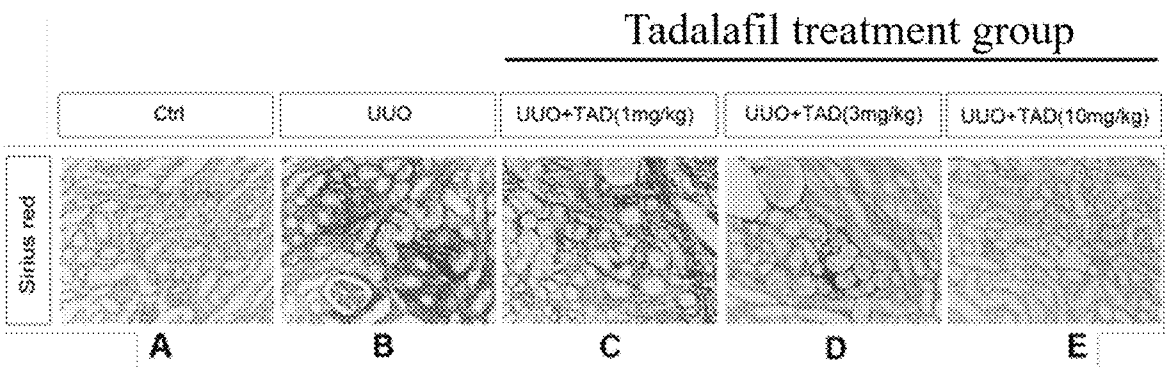
FIG. 7 is a comparison diagram (HE staining) of histological changes of glomeruli and renal tubules in left renal fibrosis lesions after treatment of UUO mice by different dosages of a PDE5 inhibitor tadalafil for 7 days, wherein A is a normal control group, B is a model group, C is a tadalafil-1 mg/kg group, D is a tadalafil-3 mg/kg group, and E is a tadalafil-10 mg/kg group.
Figure 8:
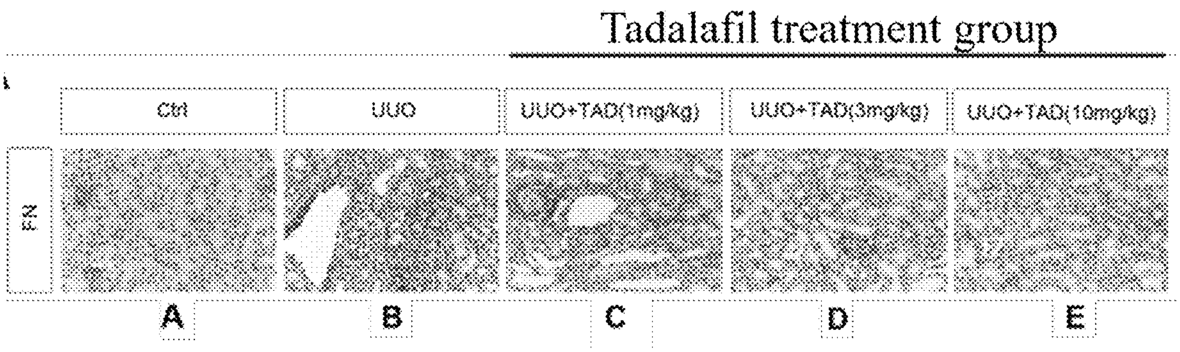
FIG. 8 shows the changes (immunohistochemistry) of the expression amount of FN in renal fibrosis lesions after treatment of UUO mice by different dosages of a PDE5 inhibitor for 7 days, wherein A is a normal control group, B is a model group, C is a tadalafil-1 mg/kg group, D is a tadalafil-3 mg/kg group, and E is a tadalafil-10 mg/kg group.
Figure 9:
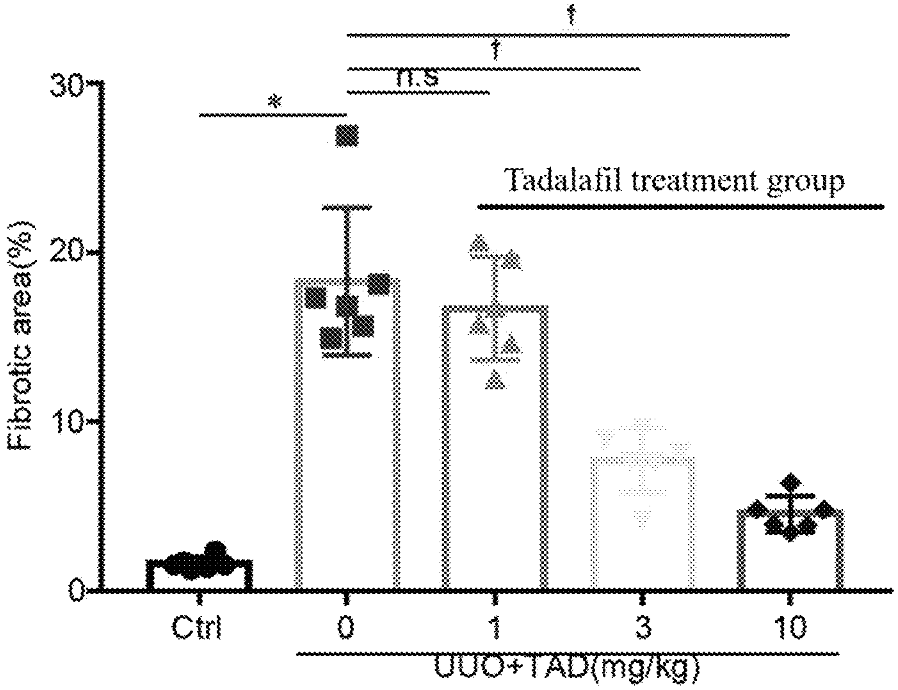
FIG. 9 is a statistical diagram of the calculated fibrotic area in left renal fibrosis lesions after treatment of UUO mice by different dosages of a PDE5 inhibitor tadalafil for 7 days.

The results of HE staining (FIG. 7) showed that in the mice of the sham operation group, the structures of kidney tissues were normal, and no pathological changes such as renal tubular atrophy or dilatation, glomerulopathy, inflammatory cell infiltration and interstitial fibrous tissue proliferation, had been seen. Compared with the mice of the sham operation group, in the mice of the UUO operation group, the renal pelvis and calyx of the kidney were obviously dilated, a large number of inflammatory cells were infiltrated in the renal interstitium, the integrity of the brush border of the renal tubules was destroyed, and there were different degrees of atrophy and necrosis, the basement membrane of the renal glomeruli became thicker, the glomerular glass-like changes were observed, collagen deposition in the renal interstitium was obvious, and the fibrotic area was significantly increased. The results of immunohistochemistry (FIG. 8) showed that the FN1 protein secreted by myofibroblasts was significantly increased in the kidney tissues of the UUO mice. After treatment with tadalafil, the infiltration of inflammatory cells in the kidney was significantly reduced, the collagen fiber proliferation in the renal interstitium was reduced, and the expression level of the FN1 protein was also significantly reduced. Compared with the UUO model group, the fibrosis areas in the renal fibrosis lesions in the tadalafil medium-dosage and high-dosage treatment groups were significantly reduced (FIG. 9).

Example 3: Effects of PDE5 Inhibitors Tadalafil and Sildenafil on Idiopathic Pulmonary Fibrosis Model Rats 1. Experimental Materials 1.1 Reagents Bleomycin hydrochloride was a product of Nippon Kayaku Co., Ltd, Japan; HPLC grade water and nintedanib (BIBF) were purchased from Shanghai Shuizheng Biomedical Technology Co., Ltd.; sodium carboxymethylcellulose was a product of Sigma Reagent Company, USA; compounds PDE5 inhibitors tadalafil and sildenafil were purchased from Apptec Co., Ltd.; and isoflurane, a pentobarbital sodium anesthetic and formalin were purchased from Sinopharm Group Co., Ltd., China.

1.2 Instruments an optical microscope camera system available from Nikon, Japan; an animal ventilator (HX-300S), a respiratory anesthesia machine (R580): RWD Life Science Co., Ltd, Shenzhen; a tissue hydroextractor: HistoCore Pearl, Leica; an embedding machine: HistoCore Arcadia, Leica; a slicer: RM2235, Leica; an automatic staining machine: LEICA Autostainer ST5020; a slice scanner: Hamamatsu NanoZoomer Digital Pathology (S210); an analytical balance: METTLERToledo, ALT104; a weighing scale: Changshu G&G Measurement Plant, T1000; an electric blanket: Jwilch, China; an operation microscope: Luckbird XTS-4A; a toe capacity measuring instrument: (Shanghai Xinruan Information Technology Co., Ltd.).

1.3 Experimental Animals

SPF-grade male SD rats. The animals were fed in a SPF-grade barrier system of an animal center of KCI Biotech (SUZHOU) Inc. (KCI). The license number of the experimental unit was SYXK (Su) 2017-0041, which followed the international standard temperature, humidity and light control system. The experimental animal operation protocol was jointly approved and confirmed by the KCI IACUC Committee. All operations and management were implemented strictly following KCI's relevant standard operating procedures (SOP).

2. Experimental Methods 2.1 Experimental Grouping 48 male SD rats were randomly divided into 6 groups according to their body weights, with 8 rats in each group: a sham operation group (Sham), a model group, a nintedanib-50 mg/kg group (BIBF-50 mg/kg), a tadalafil-5 mg/kg group, a tadalafil-20 mg/kg group, and a sildenafil-20 mg/kg group.

2.2 Animal Modeling

All the operations involved in this experiment were implemented under the guiding principle of KCI animal experiment operation SOP. After the animals were purchased, they were fed adaptively for 3-7 days before modeling. After weighing, the animals were anesthetized with isoflurane inhalation. After it was confirmed that the animals were anesthetized, the neck was sterilized, the skin of the neck was cut open, a main trachea was exposed by blunt dissection of muscle, a small incision was made between tracheal rings, a PE-20 tube was inserted into a left main bronchus, bleomycin (dosage: 3 mg/kg, volume: 1.0 ml/kg) was directly injected, and the trachea and skin were sutured. After the operation was completed, the animals were put in an electric blanket at 37° C. to keep them warm until they fully woke up, and the animals were returned into feeding cages for normal feeding after it was confirmed that they could eat and drink freely.

2.3 Dosage and Mode of Administration (i) sham operation group and model group: the mice were given normal saline by intragastric administration according to their body weights at a dosage of 1 ml·100 $g^{-1}·d^{-1}$;

(ii) nintedanib-50 mg/kg group (BIBF-50 mg/kg): BIBF was formulated into a 10 mg/ml solution with 0.5% sodium carboxymethyl cellulose, and administrated intragastrically at a dosage of 50 $mg·kg^{-1}·d^{-1}$;

(iii) tadalafil-5 mg/kg group: tadalafil was diluted into a 1 mg/ml solution with 0.5% sodium carboxymethylcellulose, and administrated intragastrically at a dosage of 5 $mg·kg^{-1}·d^{-1}$;

(iv) tadalafil-20 mg/kg group: tadalafil was diluted into a 4 mg/ml solution with 0.5% sodium carboxymethylcellulose, and administrated intragastrically at a dosage of 20 $mg·kg^{-1}·d^{-1}$;

(v) sildenafil-20 mg/kg group: sildenafil was diluted into a 4 mg/ml solution with 0.5% sodium carboxymethylcellulose, and administrated intragastrically at a dosage of 20 $mg·kg^{-1}·d^{-1}$, and the rats in each group were administrated intragastrically once a day for 14 days in total on the day of modeling.

(1) according to an interspecific dosage conversion method currently adopted by FDA, USA, the conversion coefficient of rats and human was 0.162. Therefore, according to the dosage and time of intragastric administration of tadalafil in the mice in this example, it was inferred that the oral dosage of human was 0.81-3.24 $mg·kg^{-1}·d^{-1}$, and the administration time was 14 days; and according to the dosage and time of intragastric administration of sildenafil in the mice in this example, it was inferred that the oral dosage of human was 3.24 $mg·kg^{-1}·d^{-1}$, and the administration time was 14 days.

(2) according to dosage conversion among different routes of administration in pharmacological experimental methodology, a dosage ratio of intramuscular injection and intraperitoneal injection to oral administration was about 0.3-0.4, so it was inferred that the injection dosage of tadalafil in human was 0.243-1.296 $ml·kg^{-1}·d^{-1}$, and the administration time was 14 days (medicament concentration: 1 mg/ml); and the injection dosage of sildenafil in human was 0.972-1.296 $ml·kg^{-1}·d^{-1}$, and the administration time was 14 days (medicament concentration: 1 mg/ml).

2.4 Experimental Indexes and Determining Methods 2.4.1 Weight and Volume of Left Lung of IPF Rats After 14 days of continuous administration, all animals were euthanized by intraperitoneal injection of a pentobarbital sodium anesthetic (100 mg/kg) to the animals in each group according to a KCI standard operating procedure for animal euthanasia. All animals were perfused with low-temperature PBS systematically, and then perfused systematically with formalin for fixation. The left lung was taken, and perfused with the same amount of a formalin solution, and weighed, and the subsequent lung pathogenesis related detection was carried out.

Macropathology detection of the left lung: the left lung was perfused with the same amount of the formalin solution, and then the wet weight of the left lung after perfusion was weighed with a microbalance and recorded. The volume of the left lung after perfusion was measured by a toe capacity measuring instrument and recorded.

2.4.2 Pathological Detection of Lung Tissues of IPF Rats

According to the KCI pathological standard SOP, the whole left lung was dehydrated, made into paraffin blocks, and then made into paraffin sections of the whole left lung with a section thickness of 3-4 μm. HE staining and Masson Trichrome staining were performed according to the KCI pathological standard staining SOP, and panoramic scanning of the sections was performed by a Hamamatsu NanoZoomer Digital Pathology (S210) slice scanner. The lung lesion area was calculated by subjecting the sections to Masson Trichrome staining, and the fibrotic area of the left lung (%) was the percentage of the fibrotic area in the area of the left lung. 10 visual fields with an area of 1 $mm^2$ were randomly selected in the lesion area, and pathologists performed semi-quantitative scoring under double-blind conditions according to an Ashcroft scoring system (as shown in Table 1 and FIG. 17).

TABLE 1

| Ashcroft scoring standard | |
|---|---|
| fibrosis Grading | Ashcroft scoring standard |
| 0 | Alveolar septum: no fibrosis lesion; Lung structure: normal. |
| 1 | Alveolar septum: isolated simple fibrosis changes (the thickness of the alveolar septum was increased, but was three times less than that of a normal lung); Lung structure: the alveolar cavity was partially enlarged, with a small amount of exudate, and there was no fibrotic substance. |
| 2 | Alveolar septum: definite fibrotic changes. (the thickness of the alveolar septum was increased, which was three times larger than that of a normal lung), small nodules were formed, but not connected; Lung structure: the alveolar cavity was partially enlarged, with a small amount of exudate, and there was no fibrotic substance. |
| 3 | Alveolar septum: non-intermittent fibrosis could be seen in almost all alveolar walls under each high-power field (the thickness of the alveolar septum was increased, which was three times larger than that of a normal lung); Lung structure: the alveolar cavity was partially enlarged, with a small amount of exudate, and there was no fibrotic substance. |
| 4 | Alveolar septum: alveolar septum could still be seen; Lung structure: isolated fibrotic nodules appeared in the alveolar cavity (≤10% of the high-power field). |
| 5 | Alveolar septum: alveolar septum could still be seen; Lung structure: fused fibrotic nodules appeared in the alveolar cavity (>10% and ≤50% of the high-power field), and the lung tissue structure was seriously damaged, but there was still a structure. |
| 6 | Alveolar septum: it was visible, but was almost nonexistent. Lung structure: a large number of non-intermittent fibrotic nodules appeared (>50% of the high-power field), and there was almost no lung tissue structure. |
| 7 | Alveolar septum: no longer present; Lung structure: the alveolar cavity was almost filled with fibrotic substances, but there were still less than 5 vacuole-like structures. |
| 8 | Alveolar septum: no longer present; Lung structure: under high power lens, the alveolar cavity was filled with fibrotic tissues. |

Figure 10:
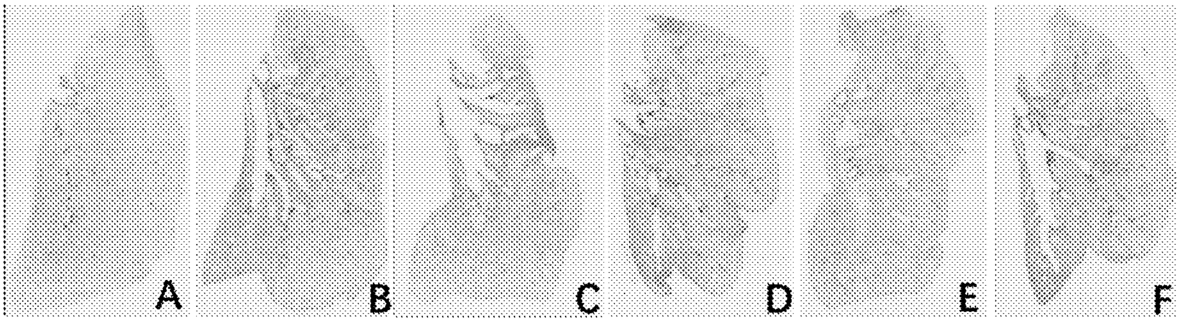
FIG. 10 is a comparison diagram (HE staining) of changes of pulmonary fibrosis lesions and lesion range in a left lung after treatment of IPF rats by different dosages of a PDE5 inhibitor and BIBF for 14 days, wherein A is a model group, B is a BIBF-50 mg/kg group, C is a tadalafil-5 mg/kg group, and D is a tadalafil-20 mg/kg group, and E is a sildenafil-20 mg/kg group.
Figure 11:
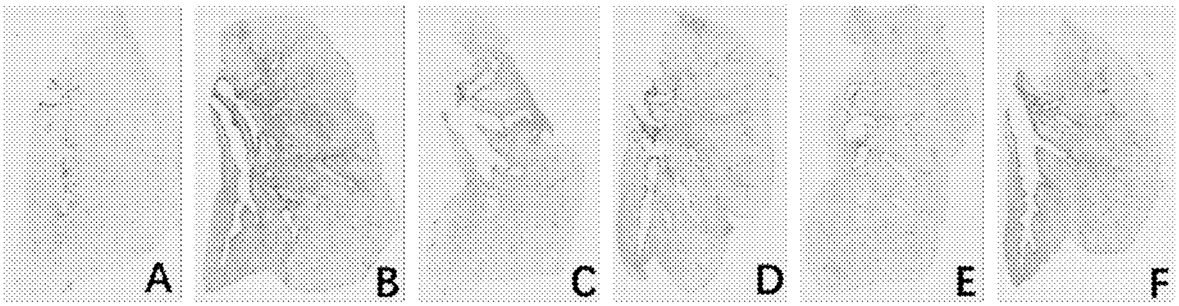
FIG. 11 is a comparison diagram (Masson Trichrom staining) of changes of pulmonary fibrosis lesions and lesion range in a left lung after treatment of IPF rats by different dosages of a PDE5 inhibitor and BIBF for 14 days, wherein A is a model group, B is a BIBF-50 mg/kg group, C is a tadalafil-5 mg/kg group, D is a tadalafil-20 mg/kg group, and E is a sildenafil-20 mg/kg group.

3. Experimental Results 3.1 Pathological Detection of the Lung Tissues at the Affected Side of the IPF Rats 3.1.1 Pulmonary Fibrosis Lesion and Lesion Range of the Left Lung The obvious lung injury with clear lung tissue boundaries could be seen from FIGS. 10-11. Two different lung histological staining (H&E and Masson Trichrom staining) clearly showed the uniform and consistent fibrosis lesion and the distribution range of the lesion in the left lung. After treatment of the IPF rats with different dosages of the PDE5 inhibitor and BIBF for 14 days, there was no significant difference in the pulmonary fibrosis lesion and lesion range in the left lung, compared with the model group.

Figure 12:
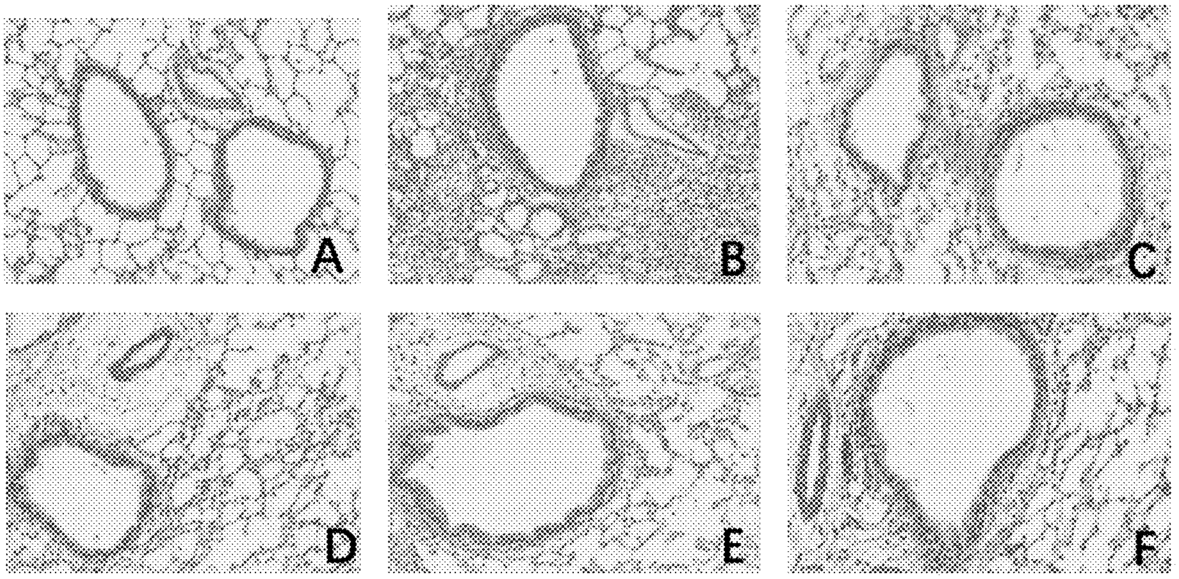
FIG. 12 is a comparison diagram (HE staining) of histological changes of bronchioles and pulmonary arterioles in pulmonary fibrosis lesions of a left lung after treatment of IPF rats by different dosages of a PDE5 inhibitor and BIBF for 14 days, wherein A is a normal lung tissue, B is a model group, C is a BIBF-50 mg/kg group, D is a tadalafil-5 mg/kg group, E is a tadalafil-20 mg/kg group, and F is a sildenafil-20 mg/kg group.
Figure 13:
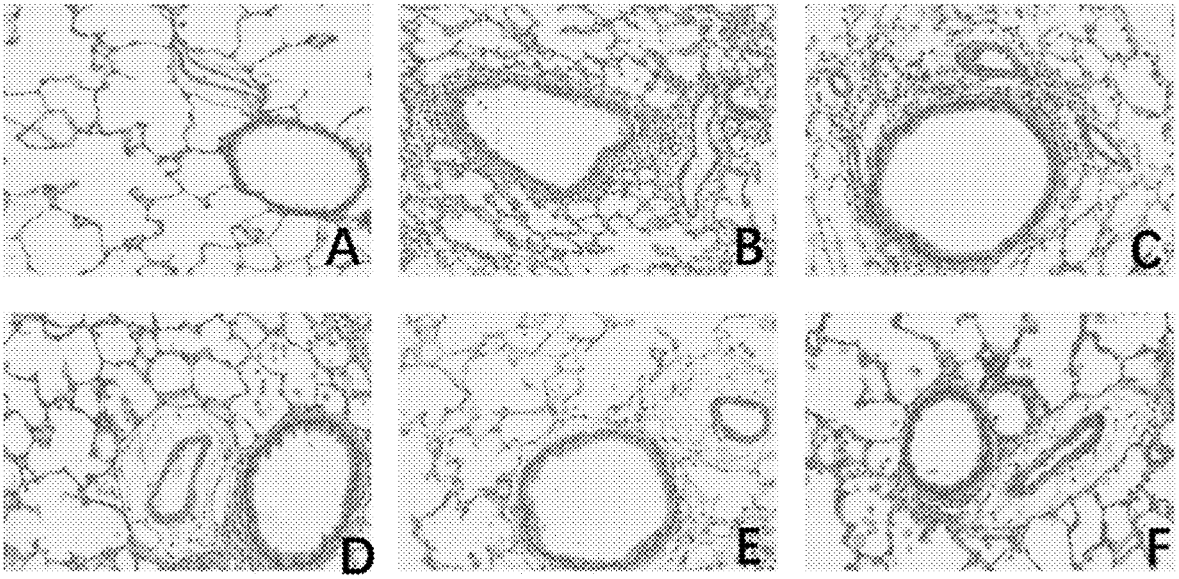
FIG. 13 is a comparison diagram (HE staining) of histological changes of bronchioles and pulmonary arterioles at the margin of pulmonary fibrosis lesions of a left lung after treatment of IPF rats by different dosages of a PDE5 inhibitor and BIBF for 14 days, wherein A is a normal lung tissue, B is a model group, C is a BIBF-50 mg/kg group, D is a tadalafil-5 mg/kg group, E is a tadalafil-20 mg/kg group, and F is a sildenafil-20 mg/kg group.

3.1.2 Histological Changes of Bronchioles and Pulmonary Arterioles in Pulmonary Fibrosis Lesion of the Left Lung of IPF Rats It was observed that epithelial cells of bronchioles, terminal bronchioles, and alveolar ducts were proliferated in different degrees, and cells in some of the epithelium and even a whole layer of the epithelium were goblet-shaped, and different amounts of mucous tissues could be seen in a lumen. Inflammatory cells were infiltrated into the tube walls of pulmonary arterioles in different degrees, the thickness of some of the tube walls was increased, and there were smooth muscle proliferation and granulation tissue proliferation on the outer membranes of the tube walls. FIG. 12 is a comparison diagram (HE staining) of histological changes of bronchioles and pulmonary arterioles in the pulmonary fibrosis lesion in the left lung after treatment of the IPF rats by different dosages of the PDE5 inhibitor and BIBF for 14 days, and FIG. 13 is a comparison diagram of histological changes of bronchioles and pulmonary arterioles at the margin of the fibrosis lesion of the left lung after treatment of the IPF rats by different dosages of the PDE5 inhibitor and BIBF for 14 days. From FIGS. 12-13, it could be seen that after treatment, the smooth muscle proliferation and inflammatory cell infiltration of bronchioles and pulmonary arterioles in the fibrosis lesion of the left lung, and bronchioles and pulmonary arterioles at the margin of the lesion were improved.

3.1.3 Injury of Alveolar Tissue in the Pulmonary Fibrosis Lesions of the Left Lung of the IPF Rats The alveolar tissues in the pulmonary fibrosis lesions of the left lung of the IPF rats were damaged in different degrees, which were exhibited as falling off and regeneration of the alveolar epithelium, the increase in the thickness of the alveolar wall and fibrosis; and different degrees of fibrous tissue deposition, inflammatory exudation and inflammatory cell infiltration in the alveolar cavity; and the lamellar alveolar structure in the fibrosis lesion was damaged and disappeared, and filled with a large number of exudative inflammatory cells and proliferated connective tissues. Inflammatory exudates and proliferated connective tissues could be seen in the remaining alveolar cavity.

Figure 14:
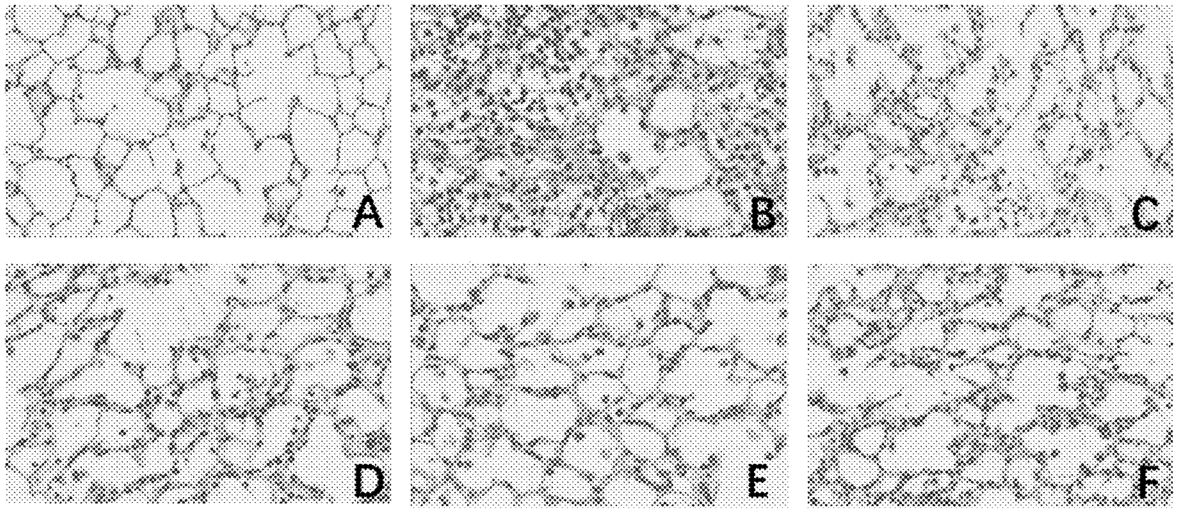
FIG. 14 is a comparison diagram (HE staining) of changes of alveolar tissue structures in pulmonary fibrosis lesions of a left lung after treatment of IPF rats by different dosages of a PDE5 inhibitor and BIBF for 14 days, wherein A is a normal lung tissue, B is a model group, C is a BIBF-50 mg/kg group, D is a tadalafil-5 mg/kg group, E is a tadalafil-20 mg/kg group, and F is a sildenafil-20 mg/kg group.

FIG. 14 is a comparison diagram (HE staining) of the changes of the alveolar tissue structure in the pulmonary fibrosis lesion of the left lung after treatment of IPF rats by different dosages of the PDE5 inhibitor and BIBF for 14 days. The results showed that: in the BIBF-50 mg/kg treatment group, some alveolar structures in the fibrosis lesion were still damaged, the thickness of the remaining alveolar wall was increased, and inflammatory cells were infiltrated into the walls; and in the tadalafil and sildenafil treatment groups, the alveolar structure in the fibrosis lesion was preserved, the thickness of the alveolar wall was increased, and inflammatory cells were infiltrated into the wall.

Figure 15:
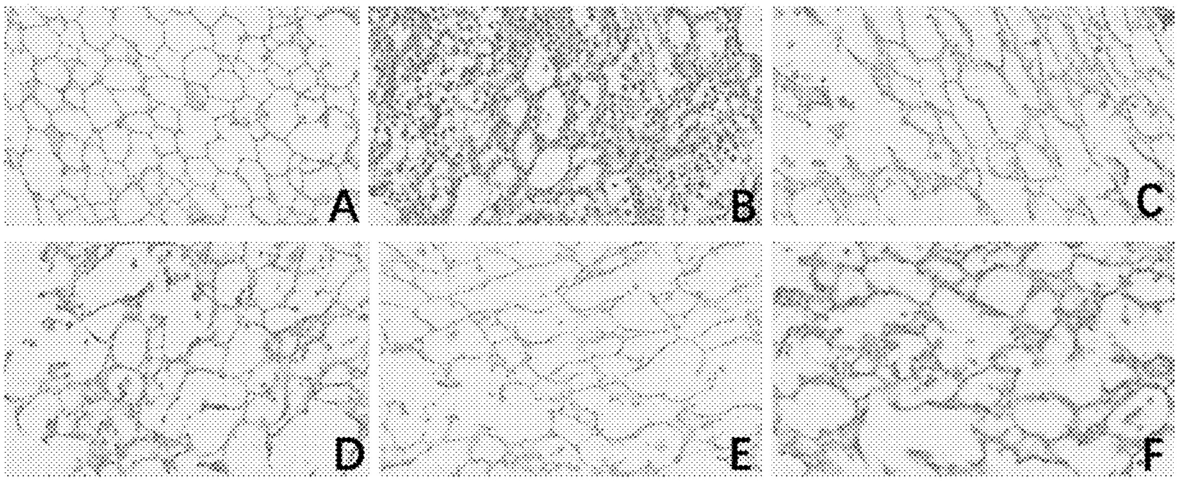
FIG. 15 is a comparison diagram (Masson Trichrom staining) of changes of alveolar tissue structures in the pulmonary fibrosis lesions of a left lung after treatment of IPF rats by different dosages of a PDE5 inhibitor and BIBF for 14 days, wherein A is a normal lung tissue, B is a model group, C is a BIBF-50 mg/kg group, D is a tadalafil-5 mg/kg group, E is a tadalafil-20 mg/kg group, and F is a sildenafil-20 mg/kg group.

FIG. 15 is a comparison diagram (Masson Trichrom staining) of the changes of the alveolar tissue structure in the pulmonary fibrosis lesion of the left lung after treatment of IPF rats by different dosages of the PDE5 inhibitor and BIBF for 14 days. The results showed that: in the BIBF-50 g/kg treatment group, some alveolar structures disappeared in the fibrosis lesion, and the thickness of the remaining alveolar wall was increased; and in the tadalafil and sildenafil treatment groups, most of the alveolar structures in the fibrosis lesion were preserved, the thickness of the alveolar wall was increased, some alveolar walls were repaired, and a small amount of inflammatory exudate was seen in the alveolar cavity.

Figure 16:
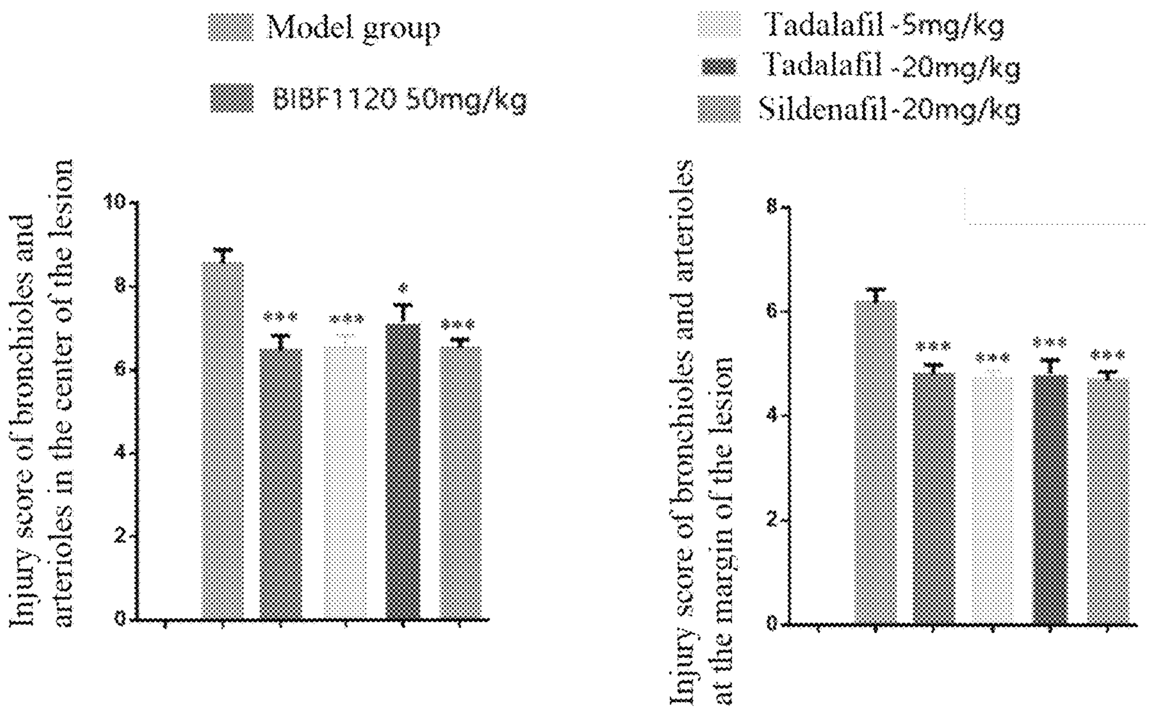
FIG. 16 shows scores of injury degree of bronchioles and pulmonary arterioles in the center and margin of pulmonary fibrosis lesions of a left lung after treatment of IPF rats by different dosages of a PDE5 inhibitor and BIBF for 14 days.

3.1.4 Scores of Injury Degree of Bronchioles and Pulmonary Arterioles in the Center and Margin of Pulmonary Fibrosis Lesion of the Left Lung of the IPF Rats FIG. 16 showed the statistics of scores of injury degrees of bronchioles and pulmonary arterioles in the center and margin of the pulmonary fibrosis lesion in the left lung after treatment of the IPF rats by different dosages of the PDE5 inhibitor and BIBF for 14 days. The results showed that: at a dosage of 50 mg/kg of a positive control drug BIBF, the scores of injury degrees of bronchioles and pulmonary arterioles in the center and margin of the pulmonary fibrosis lesion were all significantly decreased compared with those in the model group ($p<0.05$); and the scores of injury degrees of bronchioles and pulmonary arterioles in treatment groups with different dosages of the PDE5 inhibitor were also decreased significantly compared with those in the model group ($p<0.05$).

Figure 17:
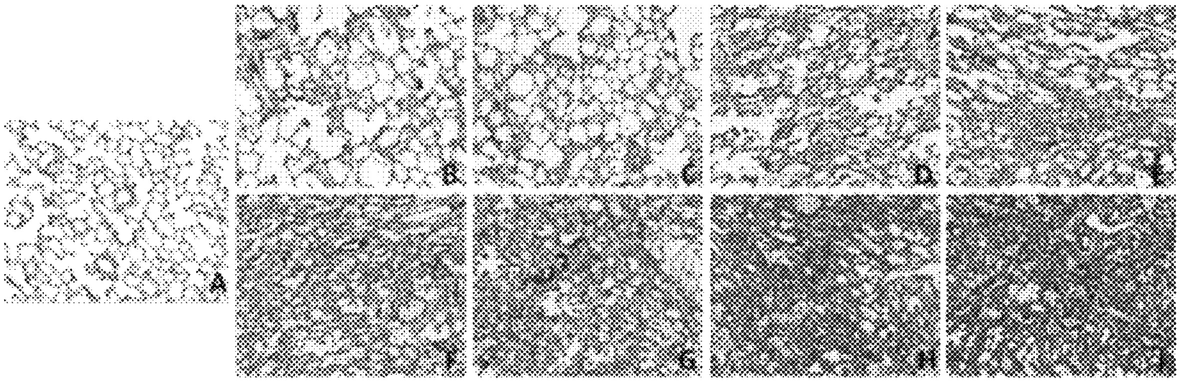
FIG. 17 shows the pathological scoring (Masson Trichrome staining) standard of pulmonary fibrosis, and Figs. A-I are sequentially pictures of Masson Trichrome staining standards of fibrosis grading 0-8 in an Ashcroft scoring system.

3.1.5 Score and Score Percentage of Pulmonary Fibrosis Lesion in the Left Lung of the IPF Rats FIG. 17 showed the pathological scoring (Masson Trichrome staining) standard of pulmonary fibrosis. After treatment of the IPF rats by different dosages of the PDE5 inhibitor and BIBF for 14 days, the changes in the scores of the pulmonary fibrosis lesion in the left lung and the changes in the percentages of the scores of the pulmonary fibrosis lesion in the left lung were statistically analyzed.

Figure 18:
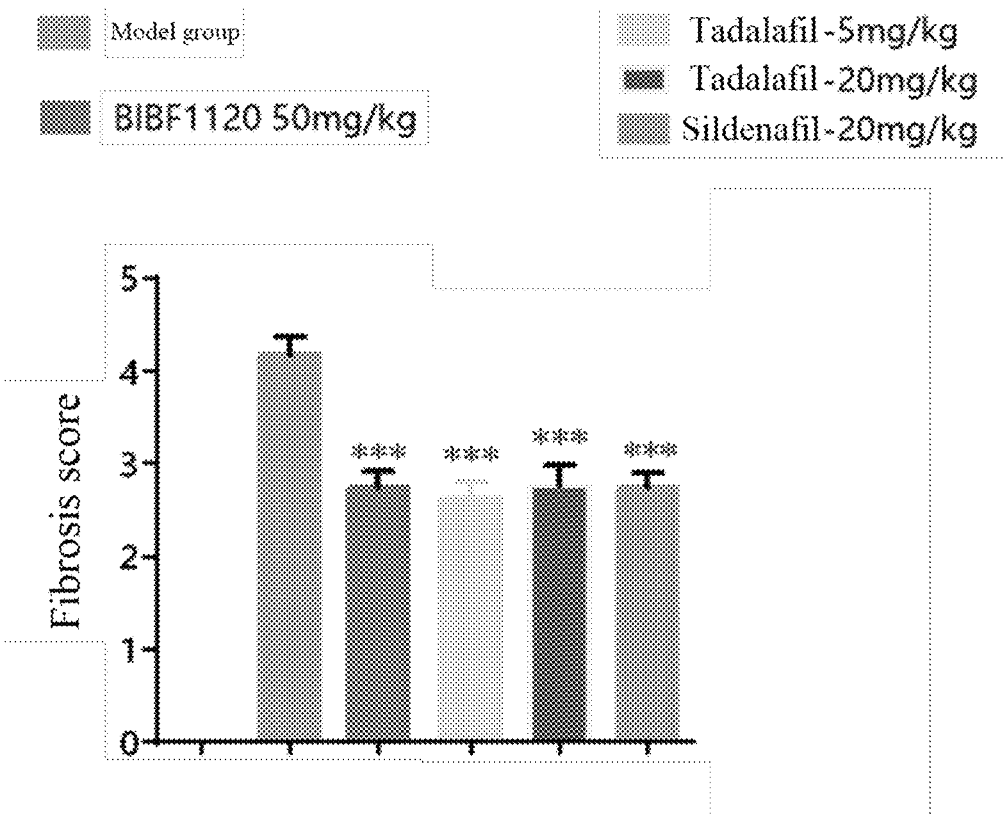
FIG. 18 is a comparison diagram of the changes of the score of pulmonary fibrosis lesions of a left lung after treatment of IPF rats by different dosages of a PDE5 inhibitor and BIBF for 14 days.

The Ashcraft scoring results of pulmonary fibrosis showed that: at a dosage of 50 mg/kg of the positive control drug BIBF, the degree of pulmonary fibrosis in the left lung of the rats was significantly improved compared with that of the model group ($p<0.05$). Oral administration of the PDE5 inhibitors tadalafil and sildenafil once a day for 14 days could significantly inhibit pulmonary fibrosis, with significant difference compared with the model group (FIG. 18, $p<0.05$).

Figure 19:
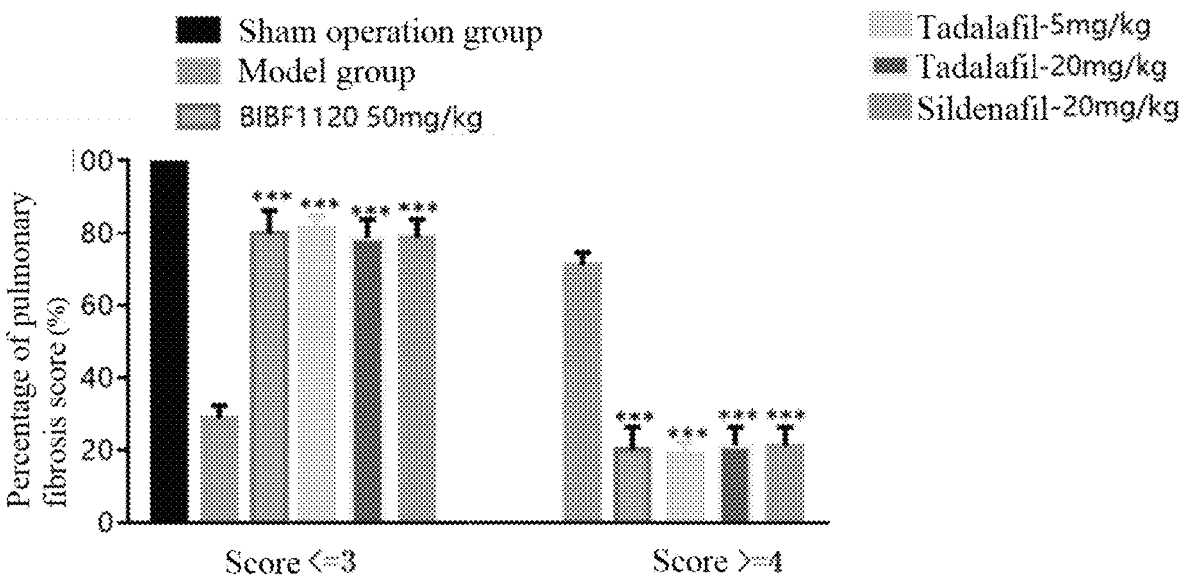
FIG. 19 is a comparison diagram of the changes of the percentage of the score of pulmonary fibrosis lesions of a left lung after treatment of IPF rats by different dosages of a PDE5 inhibitor and BIBF for 14 days.

The percentage of the pulmonary fibrosis degree scored below 3 (including 3) or above 4 (including 4) was calculated by taking an Ashcraft score of 3 as a boundary. The results of FIG. 19 showed that: nearly 51% or above of the lesion areas in the model group scored 4 or above, and after drug treatment, the lesion areas of animals in each drug treatment group scored above 4 was between 25-50%. The statistical results showed that, the percentage of the pulmonary fibrosis degree after treatment with the positive drug BIBF was significantly decreased compared with that of the model group ($p<0.05$); and the percentages of pulmonary fibrosis degrees in the treatment groups were all decreased significantly compared with that of the model group ($p<0.05$).

The aforementioned experimental results proved that the PDE5 inhibitor employed in the present disclosure could be used for treating renal fibrosis induced by ischemia-reperfusion injury (UIRI), renal fibrosis caused by unilateral ureteral obstruction (UUO) and idiopathic pulmonary fibrosis. The PDE5 inhibitor could significantly inhibit the expression of fibrosis iconic proteins in UIRI and UUO renal fibrosis lesions, improve glomerular lesions, tubular dilatation degrees, renal interstitial collagen fiber deposition and infiltration of inflammatory cells, reduce the fibrotic area in the lesion, and significantly inhibit the formation of renal fibrosis; and could effectively improve the degree of fibrosis in the idiopathic pulmonary fibrosis lesion, and relieve the damage of the alveolar structure and the proliferation of the bronchioles and pulmonary arterioles. Additionally, based on the common mechanism of organ fibrosis and the characteristics of up-regulation of expression of the fibrosis iconic proteins in fibrotic diseases, the PDE5 inhibitor described in the present disclosure could also be used for treating other fibrotic diseases such as myocardial fibrosis and hepatic fibrosis.

Obviously, the aforementioned examples are merely examples for clear explanation, and are not intended to limit the embodiments. For those of ordinary skills in the art, other different forms of changes or variations can be further made on the basis of the above description. All embodiments need not and cannot be exhaustive here. Moreover, the obvious changes or variations thus derived therefrom are still within the protection scope of the present disclosure.

What is claimed is:

1. A pharmaceutical composition for treating a fibrotic disease, comprising a phosphodiesterase type 5 inhibitor and a pharmaceutically-acceptable auxiliary material or excipient, wherein the fibrotic disease is renal fibrosis caused by renal ischemia reperfusion injury, and the phosphodiesterase type 5 inhibitor is a sildenafil analog

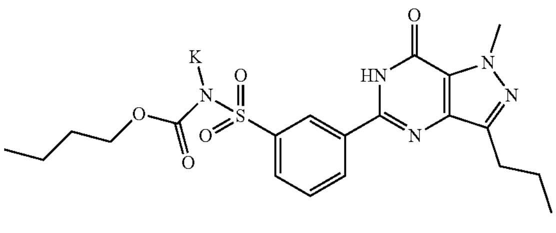

*o*, which is preferably in an oral, injection or atomized dosage form; or wherein the fibrotic disease is renal fibrosis caused by ureteral obstruction, and the phosphodiesterase type 5 inhibitor is tadalafil, which is preferably in an oral, injection or atomized dosage form; or wherein the fibrotic disease is idiopathic pulmonary fibrosis, and the phosphodiesterase type 5 inhibitor is tadalafil or sildenafil, which is preferably in an oral, injection or atomized dosage form.

2. A method for treating a fibrotic disease, comprising administering a phosphodiesterase type 5 inhibitor to a subject in need thereof, wherein the fibrotic disease is renal fibrosis caused by renal ischemia reperfusion injury, the phosphodiesterase type 5 inhibitor is a sildenafil analog

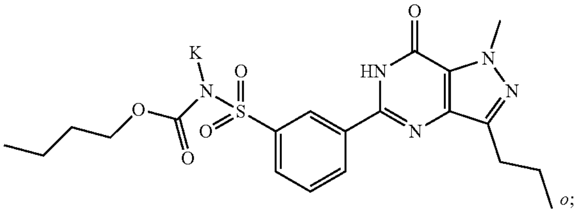

or wherein the fibrotic disease is renal fibrosis caused by ureteral obstruction, the phosphodiesterase type 5 inhibitor is tadalafil.

3. The method according to claim 2, wherein the sildenafil analog

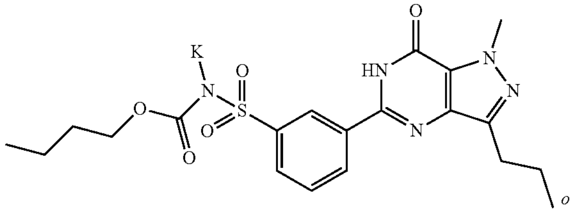

is orally administrated at a dosage of 0.405 mg·kg$^{-1}$·d$^{-1}$ for 10 days.

4. The method according to claim 2, wherein the sildenafil analog

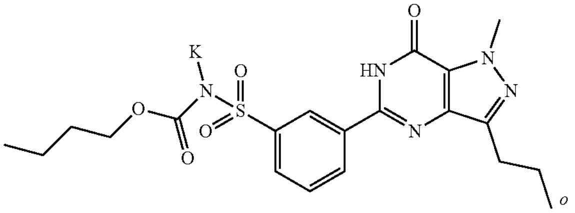

is administrated by injection at a dosage of 0.1215-0.162 ml·kg$^{-1}$·d$^{-1}$ for 10 days.

5. The method according to claim 2, wherein the tadalafil is orally administrated at a dosage of 0.081-0.81 mg·kg$^{-1}$·d$^{-1}$ for 7 days.

6. The method according to claim 2, wherein the tadalafil is administrated by injection at a dosage of 0.0243-0.324 ml·kg$^{-1}$·d$^{-1}$ for days.

7. A method for treating a fibrotic disease, comprising administering a phosphodiesterase type 5 inhibitor to a subject in need thereof, wherein the fibrotic disease is idiopathic pulmonary fibrosis, the phosphodiesterase type 5 inhibitor is tadalafil or sildenafil.

8. The method according to claim 7, wherein the tadalafil is orally administrated at a dosage of 0.81-3.24 mg·kg$^{-1}$·d$^{-1}$ for 14 days; or the sildenafil is orally administrated at a dosage of 3.24 mg·kg$^{-1}$·d$^{-1}$ for 14 days.

9. The method according to claim 7, wherein the tadalafil is administrated by injection at a dosage of 0.243-1.296 ml·kg$^{-1}$·d$^{-1}$ for 14 days; or the sildenafil is administrated by injection at a dosage of 0.972-1.296 ml·kg$^{-1}$·d$^{-1}$ for 14 days.

* * * * *